United States Patent [19]

Pastan et al.

[11] Patent Number: 5,759,782
[45] Date of Patent: Jun. 2, 1998

[54] CELLULAR APOPTOSIS SUSCEPTIBILITY PROTEIN (CSP) AND ANTISENSE CSP

[75] Inventors: Ira Pastan, Potomac; Ulrich Brinkmann, Kensington, both of Md.

[73] Assignee: The United States of America, Washington, D.C.

[21] Appl. No.: 480,662

[22] Filed: Jun. 7, 1995

[51] Int. Cl.$^6$ .................. C07H 21/00; C07H 21/04; C12N 15/63; C12N 15/09

[52] U.S. Cl. .................. 435/6; 435/320.1; 435/69.1; 435/172.3; 935/56; 935/71; 935/65; 935/62; 536/24.5

[58] Field of Search .................. 435/6, 69.1, 91.1, 435/172.3, 7.9, 320.1; 935/62, 34, 70, 71, 65, 56; 536/23.1, 23.5, 24.5

[56] References Cited

U.S. PATENT DOCUMENTS 5,585,479 12/1996 Hoke et al. .................. 536/24.5

OTHER PUBLICATIONS

Orkin, Stuart H., M.D., et al., *Report and recommendations of the Panel to Assess the NIH Investment in Research on Gene Therapy*, Dec. 7, 1995.
Cohen, J.J., "Apoptis", *Immunol. Today* 14: 126–130, 1993.
Lowe et al., "p53 is required for radiation–induced apoptosis in mouse thymocytes", *Nature* 362:847–849, 1993.
Nathan et al., "Expression of BCL-2 in primary breast cancer and its correlation with tumor pheotype", *Ann. Oncol.* 5:409–414, 1994.
Brinkmann, et al., "Expresion Cloning of cDNAs that Render Cander Cells Resistant to Pseudomonas and Diphtheria Toxin and Immunotoxins", *Molec. Med.* 1: 206–216, 1995.
Xiao, et al., "CSE1 and CEE2, Two New Genes Required for Accurate Mitotic Chromosome Segregation in *Saccharomyces cerevisiae*", *Mol. Cell. Biol.* 13: 4691–4702, 1993.
Brinkmann, et al., "B3 (Fv) –PE38KDEL, a single–chain immunotoxin that causes complete regression of a human carcinoma in mice", *Proc. Natl. Acad. Sci. USA* 88: 8616–8620, 1991.
Kochi, et al., "DNA Fragmentation and Cytolysis in U937 Cells Treated with Diphtheria Toxin or Other Inhibitors of Protein Synthesis", *Exp. Cell Res.* 208: 296–302, 1993.
Chang, et al., "Internucleosomal DNA Cleavage Precedes Diphtheria Toxin–induced Cytolysis", *J. Biol. Chem.* 264: 15261–15267, 1989.
Morimoto, et al., "Diphtheria Toxin–and Pseudomonas A Toxin–Mediated Apoptosis", *J. Immunol.* 149: 2089–2094, 1992.
Tanner et al., "Increased Copy Number at 20q13 in Breast Cancer: Defining the Critical Region and Exclusion of Candidate Genes", *Cancer Res.* 54, 4257–4260, 1994.

*Primary Examiner*—Jasemine C. Chambers
*Assistant Examiner*—Karen M. Hauda
*Attorney, Agent, or Firm*—Knobbe, Martens Olson & Bear, LLP

[57] ABSTRACT

The cDNA and amino acid sequences for a cellular apoptosis susceptibility (CAS) protein are used to detect expression and amplification of the CAS gene in normal and cancer cells. An antisense CAS gene sequence introduced into living cells inhibits CAS protein activity and thus prevents or inhibits apoptosis in the cells.

14 Claims, 12 Drawing Sheets

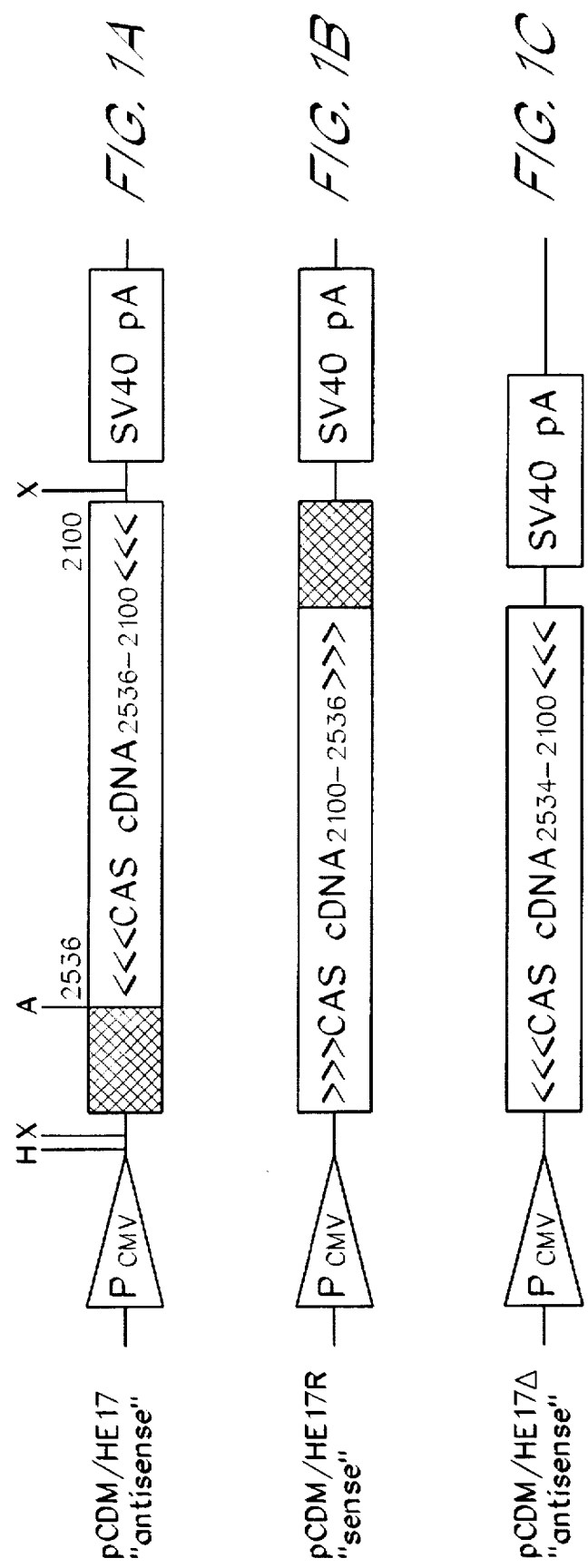

FIG. 6A. CAS cDNA SEQUENCE

```
GTCGCGCCATTTTGCCGGGGTTTGAATGTGAGGCGGAGCGGCGGCAGGAGCGGATAGTGCCAGCT
ACGGTCCGCGGCTGGGGTTCCCTCCTCCGTTTCTGTATCCCCACGAGATCCTATAGCAATGGAAC
TCAGCGATGCAAATCTGCAAACACTAACAGAATATTTAAAGAAAACACTTGATCCTGATCCTGCC
ATCCGACGTCCAGCTGAGAAATTTCTTGAATCTGTTGAAGGAAATCAGAATTATCCACTGTTGCT
TTTGACATTACTGGAGAAGTCCCAGGATAATGTTATCAAAGTATGTGCTTCAGTAACATTCAAAA
ACTATATTAAAAGGAACTGGAGAATTGTTGAAGATGAACCAAACAAAATTTGTGAAGCCGATCGA
GTGGCCATTAAAGCCAACATAGTGCACTTGATGCTTAGCAGCCCAGAGCAAATTCAGAAGCAGTT
AAGTGATGCAATTAGCATTATTGGCAGAGAAGATTTTCCACAGAAATGGCCTGACTTGCTGACAG
AAATGGTGAATCGCTTTCAGAGTGGAGATTTCCATGTTATTAATGGAGTCCTCCGTACAGCACAT
TCATTATTTAAAAGATACCGTCATGAATTTAAGTCAAACGAGTTATGGACTGAAATTAAGCTTGT
TCTGGATGCCTTTGCTTTGCCTTTGACTAATCTTTTTAAGGCCACTATTGAACTCTGCAGTACCC
ATGCAAATGATGCCTCTGCCCTGAGGATTCTGTTTTCTTCCCTGATCCTGATCTCAAAATTGTTC
TATAGTTTAAACTTTCAGGATCTCCCTGAATTTGGGAAGGTAATATGGAAACTTGGATGAATAA
TTTCCATACTCTCTTAACATTGGATAATAAGCTTTTACAAACTGATGATGAAGAGGAAGCCGGCT
TATTGGAGCTCTTAAAATCCCAGATTTGTGATAATGCCGCACTCTATGCACAAAAGTACGATGAA
GAATTCCAGCGATACCTGCCTCGTTTTGTTACAGCCATCTGGAATTTACTAGTTACAACGGGTCA
AGAGGTTAAATATGATTTGTTGGTAAGTAATGCAATTCAATTTCTGGCTTCAGTTTGTGAGAGAC
CTCATTATAAGAATCTATTTGAGGACCAGAACACGCTGACAAGTATCTGTGAAAAGGTTATTGTG
CCTAACATGGAATTTAGAGCTGCTGATGAAGAAGCATTTGAAGATAATTCTGAGGAGTACATAAG
GAGAGATTTGGAAGGATCTGATATTGATACTAGACGCAGGGCTGCTTGTGATCTGGTACGAGGAT
TATGCAAGTTTTTTGAGGGACCTGTGACAGGAATCTTCTCTGGTTATGTTAATTCCATGCTGCAG
GAATACGCAAAAAATCCATCTGTCAACTGGAAACACAAAGATGCAGCCATCTACCTAGTGACATC
TTTGGCATCAAAAGCCCAAACACAGAAGCATGGAATTACACAAGCAAATGAACTTGTAAACCTAA
CTGAGTTCTTTGTGAATCACATCCTCCCTGATTTAAAATCAGCTAATGTGAATGAATTTCCTGTC
CTTAAAGCTGACGGTATCAAATATATTATGATTTTAGAAATCAAGTGCCAAAAGAACATCTTTT
AGTCTCGATTCCTCTCTTGATTAATCATCTTCAAGCTGGAAGTATTGTTGTTCATACTTACGCAG
CTCATGCTCTTGAACGGCTCTTTACTATGCGAGGGCCTAACAATGCCACTCTCTTTACAGCTGCA
GAAATCGCACCGTTTGTTGAGATTCTGCTAACAAACCTTTTCAAAGCTCTCACACTTCCTGGCTC
TTCAGAAAATGAATATATTATGAAAGCTATCATGAGAAGTTTTTCTCTCCTACAAGAAGCCATAA
TCCCCTACATCCCTACTCTCATCACTCAGCTTACACAGAAGCTATTAGCTGTTAGTAAGAACCCA
AGCAAACCTCACTTTAATCACTACATGTTTGAAGCAATATGTTTATCCATAAGAATAACTTGCAA
AGCTAACCCTGCTGCTGTTGTAAATTTTGAGGAGGCTTTGTTTTGGTGTTTACTGAAATCTTAC
AAAATGATGTGCAAGAATTTATTCCATACGTCTTTCAAGTGATGTCTTTGCTTCTGGAAACACAC
AAAAATGACATCCCGTCTTCCTATATGGCCTTATTTCCTCATCTCCTTCAGCCAGTGCTTTGGGA
AAGAACAGGAAATATTCCTGCTCTAGTGAGGCTTCTTCAAGCATTCTTAGAACGCGGTTCAAACA
CAATAGCAAGTGCTGCAGCTGACAAAATTCCTGGGTTACTAGGTGTCTTTCAGAAGCTGATTGCA
TCCAAAGCAAATGACCACCAAGGTTTTTATCTTCTAAACAGTATAATAGAGCACATGCCTCCTGA
ATCAGTTGACCAATATAGGAAACAAATCTTCATTCTGCTATTCCAGAGACTTCAGAATTCCAAAA
CAACCAAGTTTATCAAGAGTTTTTAGTCTTTATTAATTTGTATTGCATAAAATATGGGGCACTA
GCACTACAAGAAATATTTGATGGTATACAACCAAAATGTTTGGAATGGTTTTGGAAAAAATTAT
TATTCCTGAAATTCAGAAGGTATCTGGAAATGTAGAGAAAAGATCTGTGCGGTTGGCATAACCA
ACTTACTAACAGAATGTCCCCAATGATGGACACTGAGTATACCAAACTGTGGACTCCATTATTA
CAGTCTTTGATTGGTCTTTTTGAGTTACCCGAAGATGATACCATTCCTGATGAGGAACATTTTAT
TGACATAGAAGATACACCAGGATATCAGACTGCCTTCTCACAGTTGGCATTTGCTGGGAAAAAAG
AGCATGATCCTGTAGGTCAAATGGTGAATAACCCCAAAATTCACCTGGCACAGTCACTTCACATG
TTGTCTACCGCCTGTCCAGGAAGGGTTCCATCAATGGTGAGCACCAGCCTGAATGCAGAAGCGCT
CCAGTATCTCCAAGGGTACCTTCAGGCAGCCAGTGTGACACTGCTTTAAACTGCATTTTTCTAAT
GGGCTAAACCCAGATGGTTTCCTAGGAAATCACAGGCTTCTGAGCACAGCTGCATTAAAACAAAG
GAAGTTTTCCTTTTGAACTTGTCACGAAAAAAAAAAAAAAAAAAAAAAAAAAAAAAA
```

FIG. 6B. CAS PROTEIN SEQUENCE

```
MELSDANLQT LTEYLKKTLD PDPAIRRPAE KFLESVEGNQ NYPLLLLTLL EKSQDNVIKV
CASVTFKNYI KRNWRIVEDE PNKICEADRV AIKANIVHLM LSSPEQIQKQ LSDAISIIGR
EDFPQKWPDL LTEMVNRFQS GDFHVINGVL RTAHSLFKRY RHEFKSNELW TEIKLVLDAF
ALPLTNLFKA TIELCSTHAN DASALRILFS SLILISKLFY SLNFQDLPEF WEGNMETWMN
NFHTLLTLDN KLLQTDDEEE AGLLELLKSQ ICDNAALYAQ KYDEEFQRYL PRFVTAIWNL
LVTTGQEVKY DLLVSNAIQF LASVCERPHY KNLFEDQNTL TSICEKVIVP NMEFRAADEE
AFEDNSEEYI RRDLEGSDID TRRRAACDLV RGLCKFFEGP VTGIFSGYVN SMLQEYAKNP
SVNWKHKDAA IYLVTSLASK AQTQKHGITQ ANELVNLTEF FVNHILPDLK SANVNEFPVL
KADGIKYIMI FRNQVPKEHL LVSIPLLINH LQAGSIVVHT YAAHALERLF TMRGPNNATL
FTAAEIAPFV EILLTNLFKA LTLPGSSENE YIMKAIMRSF SLLQEAIIPY IPTLITQLTQ
KLLAVSKNPS KPHFNHYMFE AICLSIRITC KANPAAVVNF EEALFLVFTE ILQNDVQEFI
PYVFQVMSLL LETHKNDIPS SYMALFPHLL QPVLWERTGN IPALVRLLQA FLERGSNTIA
SAAADKIPGL LGVFQKLIAS KANDHQGFYL LNSIIEHMPP ESVDQYRKQI FILLFQRLQN
SKTTKFIKSF LVFINLYCIK YGALALQEIF DGIQPKMFGM VLEKIIIPEI QKVSGNVEKK
ICAVGITNLL TECPPMMDTE YTKLWTPLLQ SLIGLFELPE DDTIPDEEHF IDIEDTPGYQ
TAFSQLAFAG KKEHDPVGQM VNNPKIHLAQ SLHMLSTACP GRVPSMVSTS LNAEALQYLQ
GYLQAASVTL L
```

CELLULAR APOPTOSIS SUSCEPTIBILITY PROTEIN (CSP) AND ANTISENSE CSP

FIELD OF THE INVENTION

The present invention relates to a novel gene sequence coding for a protein which is related to cell proliferation and programmed cellular death (apoptosis), and specifically relates to cDNA and amino acid sequences for this cellular apoptosis susceptibility (CAS) gene and protein.

BACKGROUND OF THE INVENTION

Apoptosis or programmed cell death is a regulated network of biochemical events which lead to cell death. It is a physiological process involved in cell differentiation, organ development and maintenance of cellular populations in multicellular organisms (Cohen, J. J., Immunol. Today 14: 126–130, 1993). Furthermore, apoptosis is a reaction to various external stimuli and cell damage (e.g. induced by drugs).

Apoptotic cells generally shrink and are phagocytosed by other cells. In contrast, necrotic cells are characterized by swelling, especially of the mitochondria which become dysfunctional, which usually results in cell lysis.

Molecular events characteristic of apoptotic cells include nuclear collapse with condensation of chromatin and loss of nucleoli. Later, the chromatin becomes fragmented into units of single or multiple nucleosomes which present a "ladder" appearance when separated by size on a gel matrix (Compton, M. M., Cancer Metast. Rev. 11: 105–119, 1992). Activation of an endogenous endonuclease causes the chromatin fragmentation. Intracellular RNA, especially mRNA, is also degraded early during apoptosis.

Apoptosis can be triggered in various ways, including virus infection, growth factor withdrawal, DNA damage resulting from irradiation, exposure to glucocorticoids and certain chemotherapy drugs, or by signals such as TNF binding to its receptor or crosslinking the Fas receptor with anti-Fas antibodies (Cohen, J. J. , Immunol. Today 14: 126–130, 1993; Williams, G. T., & Smith, C. A., Cell 74: 777–779, 1993; Suda et al., Cell 75: 1169–1178, 1993; Smith, et al., Cell 76: 959–962, 1994; Lowe et al., Nature 362: 847–849, 1993; Sentman et al., Cell 67: 879–888, 1991). The mechanism of apoptosis is not well understood, but the observed molecular changes that occur in apoptotic cells suggest that endogenous genes are responsible for apoptosis. The proteins produced from these induced genes lead to destruction of RNA and DNA ultimately leading to cell death.

Just as cell death by apoptosis is involved in normal regulation of cellular populations, cell proliferation is also required to maintain homeostasis of tissues and organs. However, in some cells, proliferation is aberrant leading to cancer. Cancer cells can be invasive, metastatic and highly anaplastic.

Although the mechanisms of tumor formation are still not completely and well defined, genetic elements, including oncogenes, have been shown to increase cell proliferation and relieve cells of normal check-points in the cell division cycle. Genes that control cell cycle check points have been identified in multicellular organisms and in yeast where they play an essential role in regulating the cell cycle. It is even possible that cell cycle check points may serve as switch points for choosing between cell proliferation and apoptosis. Thus, when a gene that controls a checkpoint is deleted, mutated, amplified in the genome, or otherwise aberrantly expressed in the cell, it may divert the cell into aberrant proliferation. Similarly, when a gene that normally controls a cell cycle switch point leading to apoptosis is aberrantly expressed, it may result in abnormal cell proliferation.

Some mammalian genes and proteins that have been simultaneously implicated in the regulation of cell proliferation and apoptosis including the genes for p53, BCL-2 or Myc. Although the pathways leading to apoptosis have not been fully elucidated, several genes that play a role in apoptosis have also been shown to play an important role in cancer. The p53 gene, coding for a tumor suppressor, is required for radiation-induced apoptosis (Lowe et al., Nature 362: 847–849, 1993). BCL-2 inhibits apoptosis in many cells (Sentman et al., Cell 67: 879–888, 1991; Vanhaesebroeck et al., Oncogene 8: 1075–1081, 1993) and furthermore, increased BCL-2 gene expression has been detected in primary breast cancer tissue without bcl-2 gene amplification (Nathan et al., Ann. Oncol. 5: 409–414, 1994).

Apoptosis can also be induced by exposing cells to Diphtheria toxin (DT) or Pseudomonas toxin (PE) (Kochi, S. K., and Collier, R. J., Exp. Cell Res. 208: 296–302, 1993; Chang, M. P., et al., J. Biol. Chem. 264: 15261–15267, 1989; Morimoto, H., and Bonavida, B., J. Immunol. 149: 2089–2094, 1992). Both of these bacterial toxins inhibit eukaryotic protein synthesis by inactivating elongation factor 2 by ADP-ribosylation (Carroll, S. F. and Collier, R. J., J. Biol. Chem. 262: 8707–8711, 1987). Although the toxin-specific mechanism by which these toxins induce apoptosis is unknown, it is not simply due to inhibition of protein synthesis because other protein synthesis inhibitors do not induce apoptosis (Chang, M. P., et al., J. Biol. Chem. 264: 15261–15267, 1989; Morimoto, H., and Bonavida, B., J. Immunol. 149: 2089–2094, 1992).

SUMMARY OF THE INVENTION

According to one aspect of the invention, there is provided a purified and isolated cDNA coding for a human CAS protein having the sequence of SEQ ID NO:1.

According to another aspect of the invention, there is provided a purified and isolated cDNA sequence coding for a portion of a human CAS protein consisting of nucleotides 2100 to 2536 of SEQ ID NO:1.

According to another aspect of the invention, there is provided a purified and isolated human CAS protein having of the amino acid sequence of SEQ ID NO:2.

According to yet another aspect of the invention, there is provided a purified and isolated human CAS protein consisting of the amino acid sequence corresponding to amino acids at positions 700–845 of SEQ ID NO:2.

According to yet another aspect of the invention, there is provided a method of detecting cancerous cells, comprising measuring expression of a human CAS gene at a level higher than expression of a CAS gene in normal noncancerous human cells. In one embodiment of the method, the CAS gene expression is measured by detecting the level of CAS mRNA in cells. The CAS mRNA can be detected by hybridization with a complementary DNA or by a polymerase chain reaction. In another embodiment, CAS gene expression is measured by detecting the level of CAS protein in cells. In a preferred embodiment, the CAS protein is detected by binding of antibody that recognizes CAS protein.

According to another aspect of the invention, there is provided a method of detecting cancer cells, including measuring the number of copies of a CAS gene present in cells. In this method, the number of copies of a CAS gene is higher in cancer cells than the number of copies of a CAS gene in normal noncancer cells. In one embodiment of the method, the number of copies of a CAS gene is measured by detecting the amount of hybridization of a DNA complementary to SEQ ID NO:1 or any portion of 25 or more nucleotides therein. In another embodiment, the method further includes measuring the number of copies of a single copy gene present in both cancerous and normal noncancerous cells and comparing the number of the single copy gene to the number of copies of a CAS gene in both cancerous and normal noncancerous cells. In a preferred embodiment, the single copy gene is an actin gene. In another embodiment of the method, the number of copies of a CAS gene is determined by a polymerase chain reaction that amplifies either a 5' portion of the CAS gene, a 3' portion of the CAS gene, or both a 5' and a 3' portion of the CAS gene. In preferred embodiments of the method, the cancer cells are breast tissue cells or colon cells.

According to another aspect of the invention, there is provided a method of treating cancer in a mammal in need of treatment, including administering to the mammal an agent that decreases CAS protein activity in cells. In one embodiment of the method, the agent is an antibody that recognizes CAS protein. In another embodiment of the method, the agent is an antisense CAS gene sequence that inhibits CAS protein activity by decreasing expression of a CAS gene. In a preferred embodiment, the agent is an antisense CAS gene sequence consisting of nucleotides 2100 to 2536 of SEQ ID NO:1. In preferred embodiments of the method in which the agent is an antisense CAS gene sequence, the antisense CAS gene sequence is in a vector that includes genetic elements that regulate transcription of said antisense CAS gene sequence, including a promoter sequence and a poly-A signal.

According to another aspect of the invention, there is provided a purified and isolated antisense CAS gene sequence consisting of nucleotides 2100 to 2536 of SEQ ID NO:1.

According to yet another aspect of the invention, there is provided a kit for diagnosing cancer, comprising an antibody that recognizes CAS protein and means for indicating binding of the antibody to the CAS protein.

According to another aspect of the invention, there is provided a kit for diagnosing cancer, comprising polynucleotides that serve as primers in a polymerase chain reaction for direct amplification of a nucleic acid coding for CAS protein and one or more reagents for performing a polymerase chain reaction or reagents for detecting a product of the polymerase chain reaction.

According to another aspect of the invention, there is provided a purified and isolated antibody that specifically recognizes CAS protein In one embodiment, the antibody is made using the DNA sequence of SEQ ID NO:1 or any portion thereof to produce an antigenic protein or peptide.

According to another aspect of the invention, there is provided a method for preventing or reversing apoptosis in a mammalian cell, including the steps of providing the CAS gene DNA sequence of SEQ ID NO:1 in a vector such that an antisense CAS transcript will be made under the regulation of DNA sequences contained within said vector, and administering an effective amount of the vector containing SEQ ID NO:1 to a mammalian cell thereby delivering the vector intracellulary.

It should be understood that both the foregoing general description and the following detailed description are exemplary and explanatory only and are not restrictive of the invention as claimed. The accompanying drawings, which are incorporated in and constitute a part of the specification, illustrate various embodiments of the invention and, together with the description, serve to explain the principles of the invention.

BRIEF DESCRIPTION OF THE DRAWINGS

FIG. 1 is a diagram of three plasmids showing the CAS cDNA clones in the "antisense" (FIG. 1A, pCDM/HE17) and "sense" (FIG. 1B, pCDM/HE17R) directions containing unrelated DNA (shadowed), and in the "antisense" direction (FIG. 1C, pCDM/HE17A) without the unrelated DNA.

FIGS. 6A–6B shows the DNA sequence of the CAS cDNA (FIG. 6A, SEQ ID NO:1) and the corresponding amino acid sequence (FIG. 6B; SEQ ID NO:2).

DETAILED DESCRIPTION OF THE INVENTION

Figure 2A:
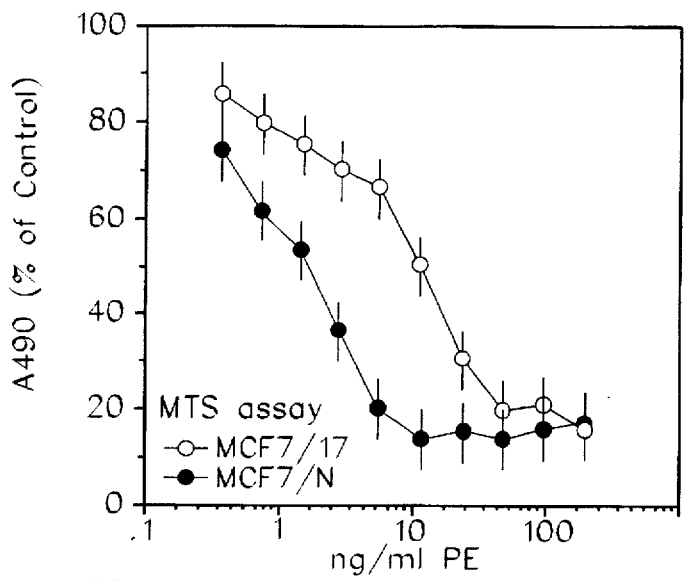
FIG. 2A–2F shows that CAS antisense reduces the sensitivity of MCF-7 cells to PE as determined by the MTS assay (FIG. 2A and 2B), even though protein synthesis is inhibited (FIG. 2C), and by time course experiments in which antisense tranfectants undergo growth arrest upon toxin treatment but recover after removal of toxin (FIG. 2D–2F).

Diphtheria toxin (DT) and Pseudomonas toxin (PE) are toxins that affect ADP-ribosylation that have been used to make recombinant immunotoxins that can specifically target and kill cancer cells in vitro and in vivo (Brinkmann, U., et al., *Proc. Natl. Acad. Sci. USA* 88: 8616–8620, 1991; Pastan I., et al., *Annu. Rev. Biochem.* 61: 331–354, 1992; Brinkmann U., and Pastan I., *Biochem. Biophys. Acta.* 1198: 27–45, 1994). However, it is known that for other anticancer agents, treated cells can become drug resistant causing the drugs to loose their efficacy (Schimke, R. T., *Cell* 37: 705–713, 1988; Gottesman, M. M., and Pastan, I., *Annu.*

*Rev. Biochem.* 62: 385–427, 1993). Several known mechanisms by which cells can become resistant to ADP-ribosylating toxins, and thus possibly also to anti-cancer immunotoxins, include altered toxin binding, internalization, processing, and alterations in elongation factor 2 (EF2), the intracellular toxin target (Laurie and Robbins, 1991; Kido et al., 1991; Fendrick et al., 1992; Chaudhary et al., 1990).

We have used expression cloning to isolate cDNA-containing plasmids that cause breast cancer cells (e.g., cell line MCF-7) to become immunotoxin-resistant (Brinkmann, U., et al., *Molec. Med.* 1: 206–216, 1995). Using this approach, we isolated a gene that renders cells resistant to PE and DT. Because PE and DT induce apoptosis, the resistance of cells containing these clones suggested that the cloned cDNA was related to regulation of apoptosis. Hence we named the gene "CAS" for Cellular Apoptosis Susceptibility, in reference to the function of the protein product of the gene. Plasmids containing even a portion of the CAS gene rendered the MCF-7 cells resistance to native PE and DT, indicating that the resistance was due to interference with the action of the toxin moiety rather than another portion of the immunotoxins.

In cells transfected with the CAS clones, the cells did not die upon exposure to PE or DT, even though the toxins caused modification of EF2 and inhibition of protein synthesis comparable to toxin-sensitive control cells. Thus, these clones represent a class of genes that determine the sensitivity of cells to toxin after inhibition of protein synthesis, the primary action of the toxins, has occurred. The isolated and purified cDNA coding for the CAS protein is the subject of this invention.

The clone that mediated PE- and DT-resistance of transfected MCF-7 cells, without interfering with ADP-ribosylation of EF2 and subsequent inhibition of protein synthesis, contains an antisense CAS cDNA fragment. MCF-7 cells containing the antisense CAS cDNA clone were less susceptible to toxin induced apoptosis and apoptosis induced by TNF-alpha and TNF-beta. These results show that the gene has a function in apoptosis. Independent from that function in apoptosis, we found that expression of the human CAS gene was elevated in tissues containing many dividing cells and in tumor cell lines, indicating that CAS also has a role in cell proliferation. The CAS gene sequence is partially homologous with that of the yeast CSE1 gene, which plays a role in yeast cell division (Xiao, Z., et al., *Mol. Cell. Biol.* 13: 4691–4702, 1993).

The present invention includes a complete cDNA sequence coding for CAS protein and the corresponding complete amino acid sequence of CAS protein. The sequences are useful for making purified CAS protein which can be used to develop protein-based kits for detection of CAS protein, a potential marker for cancer, in human cells and tissue. The DNA sequence, in whole or part, can be used as a probe to detect gene expression and genetic rearrangements of the CAS gene and the surrounding chromosomal region. This is useful for diagnosing cancer and determining its degree of malignancy based on CAS gene expression or genetic rearrangement. This aspect is especially important in diagnosing and treating cancer by indicating the physiological condition of cancerous cells thus allowing a clinician to administer an appropriate treatment for the detected cancer. The sequence may be useful as an antisense therapeutic composition for decreasing functional CAS expression intracellularly and thus controlling growth of malignant cells or tissue. The sequence may also allow one to induce abnormal physiological conditions in a mammal by overexpressing the CAS gene to create animal models for human pathological conditions (e.g., breast and colon cancer) which are useful for discovery of new therapeutics to improve the current treatments of these conditions.

The general principles of the present invention may be more fully appreciated by reference to the following non-limiting examples.

EXAMPLE 1

ISOLATION OF A cDNA CLONE THAT RENDERS A BREAST CANCER CELL LINE RESISTANT TO CELL DEATH INDUCED BY TOXINS

Expression cloning and immunotoxin selection of cDNA plasmids. A cDNA library in plasmid pCDM8 that contains HeLa cDNA expressed from a CMV promoter and followed by a SV40 polyA sequence was obtained from Clontech and transfected into MCF-7 breast carcinoma cells. Clones of human cDNAs that confer resistance to the immunotoxin B3 (Fv)-PE38KDEL were isolated by expression cloning and selection (Brinkmann, U., et al., *Molec. Med.* 1: 206–216, 1995) with the immunotoxin B3 (Fv) -PE38KDEL, a fusion protein composed of a truncated form of PE and the Fv region of monoclonal antibody (MAb) B3 that binds to a carbohydrate present on many carcinomas and cancer cell lines, including MCF-7 cells, and kills them (Brinkmann, U., et al., *Proc. Natl. Acad. Sci. USA* 88: 8616–8620, 1991).

Briefly, MCF-7 cells expressing the SV40 T antigen, which allows episomal replication in the cells, (MCF-7/T; Brinkmann, U., et al., *Molec. Med.* 1: 206–216, 1995) were transfected with a HeLa cDNA expression library and treated two days later with high doses of B3 (Fv) -PE38KDEL (Brinkmann, U., et al., *Proc. Natl. Acad. Sci. USA* 88: 8616–8620, 1991). Dead cells were removed by washing with phosphate buffered saline (PBS), the remaining cells harvested, and plasmids were recovered (Hirt, B., *J. Mol. Biol.* 26: 365–369, 1967). The recovered plasmids were propagated and amplified in *E. coli* (strain MC1061/P3) using 35–50 µg/ml ampicillin and 12.5–15 µg/ml tetracycline. Plasmid DNA for transfections was purified by standard techniques well known in the art based on elution from DEAE-Sephacel (using a Qiagen™ "Mega" plasmid DNA preparation kit) and retransfected into MCF-7/T for two additional rounds of immunotoxin-selection and plasmid reisolation as described above. Using this procedure, plasmids that caused cells to survive after immunotoxin exposure were selectively enriched resulting in siblings of the same or overlapping cDNAs in the final plasmid pool analyzed. Such plasmids were identified by DNA hybridization analysis and several plasmids were found that were present more than once in a pool of 96 individual plasmid clones randomly isolated after three rounds of immunotoxin selection.

These toxin-resistance clone candidates were stably transfected into MCF-7 cells and analyzed individually for their effects on toxin sensitivity (as described in Brinkmann, U., et al., *Molec. Med.* 1: 206–216, 1995). Cell line MCF-7/17 that contains a plasmid, pCDM/HE17, (called "p17" in Brinkmann, U., et al., *Molec. Med.* 1: 206–216, 1995) was obtained by cotransfection with another plasmid, pMC1neo/polyA, that confers resistance to the drug G418 which was used to select transformants using standard tissue culture methods.

Molecular manipulations of clones. pCDM/HE17 was isolated from that library by immunotoxin selection and contains a 700 bp insert composed of 436 bp of antisense cDNA called CAS and 264 bp of unrelated sequence (FIG. 1). The CAS gene was identified as an open reading frame with homology to a yeast gene, CSE1 (Xiao, Z., et al., *Mol. Cell. Biol.* 13: 4691–4702, 1993). Standard cloning techniques (Sambrook, J., et al., *Molecular cloning. A Laboratory Manual.*, 2nd ed., 1989) were used to make pCDM8/HE17R, a plasmid containing the 700 bp cDNA in an inverse orientation, and pCDM8/HE17Δ, a plasmid in which a 260 bp Asp700-HindIII fragment that is not homologous to a CSE1 sequence has been deleted.

The relevant portions of these three plasmids are diagrammed in FIG. 1. Plasmid pCDM/HE17 contains a 700 bp insert composed of 436 bp antisense cDNA (open box), which is homologous to the yeast CSE1 gene, and 264 bp unrelated sequence (shadowed box) in an antisense direction behind the CMV promoter followed by the SV40 poly-A signal. X,A and H indicate XbaI, Asp700 and HindIII sites. pCDM/HE17R contains the cDNA (XbaI-fragment) of pCDM/HE17 in reverse orientation and pCDM8/HE17Δ has the 260 bp Asp700-HindIII non-CSE1 fragment deleted. As negative controls, four plasmids containing unknown inserts (pCDM8/C2-pCDM8/C5) were randomly chosen from the same library.

Recombinant MCF-7 cell lines. Cell lines were produced by electroporation of $5 \times 10^6$ MCF-7 cells with 3 µg pMC1neo/polyA and 15 µg of expression plasmid, using a Biorad™ gene pulser at 400 V, 960 FD, in 0.4 cm cuvettes (as described in Brinkmann, U., et al., *Molec. Med.* 1: 206–216, 1995). MCF-7/T cells are a pool of MCF-7 cells that express SV40 large T antigen, thus allowing episomal replication of plasmids with an SV40 origin (e.g., pCDM8). MCF-7/T cells were made by cotransfection of pCMV-TAg (Ogryzko, V. V., et al., *J. Virol.* 68: 3724–3732, 1994) and pMC1neo/polyA and selection of a transfected cell pool with 0.8 mg/ml G418 (FIG. 1A). Similarly, MCF-7/17, MCF-7/17R and MCF-7/17Δ cell pools were produced by cotransfection of pMC1neo/polyA and 15 µg of pCDM/HE17, pCDM/HE17R or pCDM/HE17Δ, respectively. MCF-7/C and MCF-7/C2-C5 cells were produced by cotransfection of pMC1neo/polyA with pCDM8 (vector alone, to produce MCF-7/C cells) or pCDM/C2-C5 (to produce MCF-7/C2-C5 cells), control plasmids randomly chosen from the library without any selection. MCF-7/N cells contained only pMC1neo/polyA. All these cell lines were selected and propagated with media containing 0.8 mg/ml G418 and were not exposed to toxins or TNF until their response to these agents was tested.

One clone that conveyed immunotoxin resistance on MCF-7 breast cancer cells is pCDM/HE17, a plasmid containing a 700 bp HeLa cDNA insert (FIG. 1). This clone rendered MCF-7 cells about 10-fold less sensitive to a PE-derived immunotoxin as well as to native PE and DT (Brinkmann, U., et al., *Molec. Med.* 1: 206–216, 1995). Both toxins usually cause cell death by inactivating EF2 (by ADP-ribosylation of the protein), thereby arresting protein synthesis. Although cells containing clone pCDM/HE17 were resistant to PE and DT, they were not resistant to ricin or cycloheximide which inhibit protein synthesis by other mechanisms (Brinkmann, U., et al., *Molec. Med.* 1: 206–216, 1995).

The cDNA insert in plasmid pCDM/HE17 was determined using fluorescently labeled dideoxynucleotides essentially according to the method of Sanger et al. (*Proc. Natl. Acad. Sci. USA* 74: 5463 1977) using an automated sequencer (ABI™ model 373A and the ABI™ Dyedeoxy Terminator kit).

The DNA sequence of pCDM/HE17 cDNA revealed a 436 bp cDNA fragment that is part of a previously unidentified human homolog of the yeast CSE1 chromosome segregation gene (Xiao, Z., et al., *Mol. Cell . Biol.* 13: 4691–4702, 1993), which we call CAS. The human CAS cDNA clone has 45% protein identity and 66% similarity of amino acids when compared to the yeast CSE1 sequences (Xiao, Z., et al., *Mol. Cell. Biol.* 13: 4691–4702, 1993) in this portion of the DNA (discussed in detail in Example 9). Plasmid pCDM8/HE17 also contains 264 bp of an unrelated sequence fused to CAS sequences. This is library-ligation artifact because this sequence is not related to the sequence of the full length CAS isolated from human placenta cDNA (discussed in Example 7) and also not linked to the gene in HeLa cells, as shown by hybridization of Southern blots of HeLa and placenta DNA cleaved with various enzymes. This unrelated sequence does not have any open reading frame and therefore is noncoding, and its expression was not detected by Northern blot analysis of RNA from any human tissue. The CAS clone is present in an "inverse" orientation so that transcription from the CMV promoter of pCDM/HE17 generates an antisense RNA. Therefore, the resistance mediated by pCDM/HE17 is likely due to antisense RNA produced from this partial CAS gene sequence which interferes with expression of the human CAS gene.

EXAMPLE 2

CELLULAR RESISTANCE TO TOXINS IS MEDIATED BY CAS ANTISENSE RNA

To confirm that toxin resistance mediated by clone pCDM/HE17 is caused by antisense RNA production of CAS RNA, a plasmid (called pCDM/HE17R; see FIG. 1B) was constructed in which the insert of pCDM/HE17 was inverted so that sense RNA fragment would be made from the plasmid. This plasmid did not render cells resistant. To rule out a possible effect of the additional non-CAS sequence, the 264 bp sequence that showed not homology to the yeast CSE1 gene was also deleted, to produce plasmid pCDM/HE17Δ (FIG. 1). These plasmids were individually cotransfected with plasmid pMC1neo/polyA into MCF-7 cells and stably transfected cells containing pMC1neo/polyA and each of these plasmids were isolated. Additional controls were MCF-7 cells cotransfected with pMC1neo/polyA and the library vector pCDM8 without insert (called MCF-7/C), MCF-7 cells with randomly chosen plasmids from the unselected pCDM8/HeLa library (called MCF-7/C2-C5), and MCF-7 cells with pMC1neo/polyA alone (called MCF-7/N). Cells were propagated using G418-resistant drug selection. Cells were not exposed to toxin until their response to toxins was analyzed. All transfectants (including the parent clone, MCF-7/17) were pooled transfectants (greater than 10 colonies) rather than isolated single clones to compensate for possible clonal variability in the cells containing the transfected plasmids (Brinkmann, U., et al., *Molec. Med.* 1: 206–216, 1995).

FIG. 2 shows experiments in which the sensitivity to PE of MCF-7 cells and CAS antisense transfected MCF-7 cells was analyzed using the MTS cell proliferation assay. PE was chosen to represent ADP-ribosylating toxins (which also include immunotoxins and DT) in this study because the relative sensitivities or resistance of the cell lines to PE, DT and immunotoxins were comparable, i.e., cells resistant to PE also were resistant to immunotoxin as well as to DT (Brinkmann, U., et al., *Molec. Med.* 1: 206–216, 1995).

Sensitivity to PE was assayed by MTS assays (Cory, A. H., et al. *Cancer Commun.* 3: 207–212, 1991) which detect dehydrogenases present in living cells (using absorbance at 490 nm which is proportional to number of live cells), or by assaying incorporation of $^3$H-leucine into cellular proteins (protein synthesis inhibition assay; Brinkmann, U., et al., *Proc. Natl. Acad. Sci. USA* 88: 8616–8620, 1991). Usually $3\times10^3$ cells/well in 200 µl medium were plated and grown overnight, incubated with toxin for 20 hrs (or as indicated), and then assayed. Referring to FIG. 2, the symbols are the same for all experiments. MCF-7/17 cells (O) and MCF-7/17Δ cells (Δ) contained CAS antisense clones. Controls were MCF-7/N cells (●) which contained only the pMC1neo/polyA plasmid and MCF-7/C cells (■) which contained pMC1neo/polyA and the pCDM8 library vector without insert. The MCF-7/17R cells (▲) contained CAS cDNA in the sense direction (see FIG. 1 for diagrams of the plasmids with CAS inserts).

FIG. 2A shows an experiment in which cells were exposed to various concentrations of PE for 3 days and the number of cells present on day 3 was measured by the MTS assay. It is evident that MCF-7/17 cells containing CAS antisense were about 10-fold more resistant to PE than the control cell lines (MCF-7/N) and MCF/C, with an $IC_{50}$ of about 15 ng/ml compared to 1–2 ng/ml in the control. To eliminate the possibility that the additional non-CAS sequence influences toxin sensitivity, MCF-7/17Δ cells containing CAS antisense without the additional sequence were also tested.

Figure 2B:
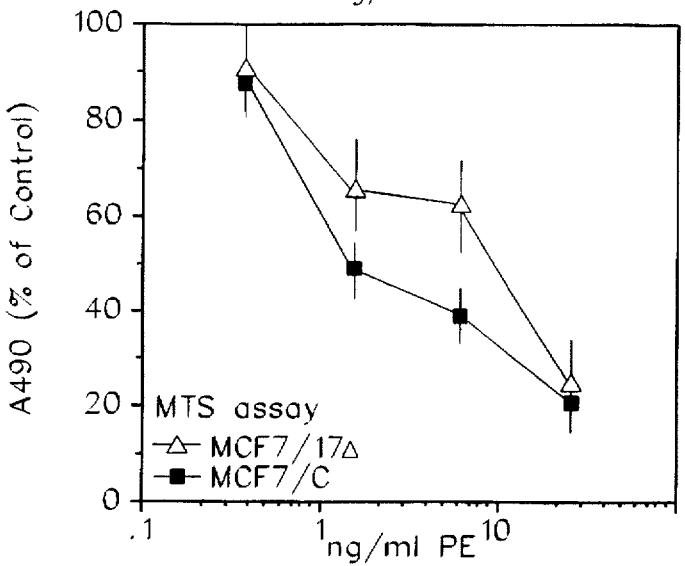

FIG. 2B shows that these cells were also more resistant to PE, although the resistance was not as pronounced as with MCF-7/17. These experiments show that the presence of CAS antisense reduces the sensitivity of MCF-7 cells towards PE.

Figure 2C:
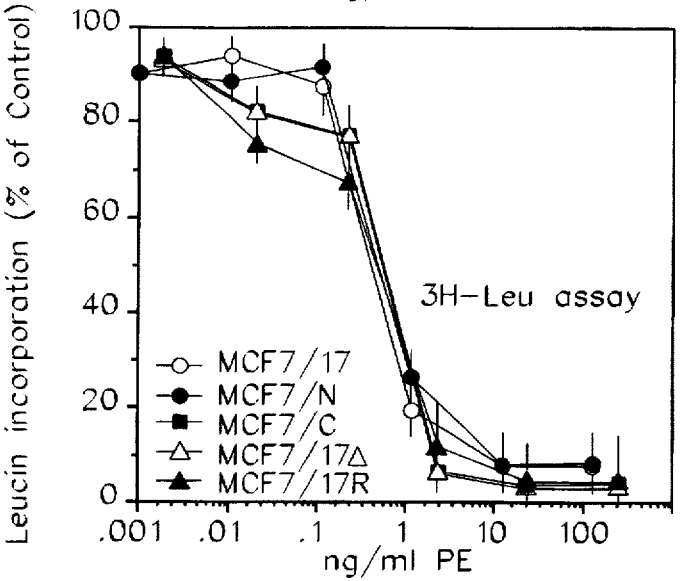

FIG. 2C shows inhibition of protein synthesis, assayed by measuring the incorporation of $^3$H-leucine 20 hrs after toxin addition. All cells tested showed the same amount of inhibition of protein synthesis indicating that the PE entered the cells and inactivated EF2, its normal cellular target.

Figure 2D:
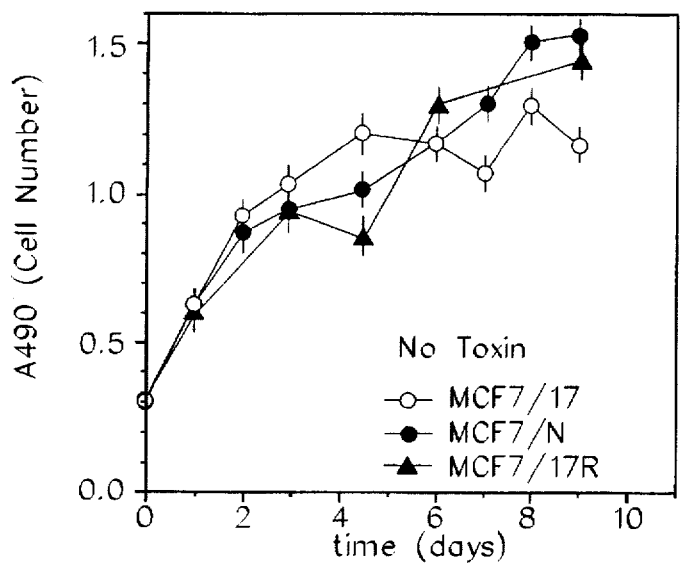
Figure 2E:
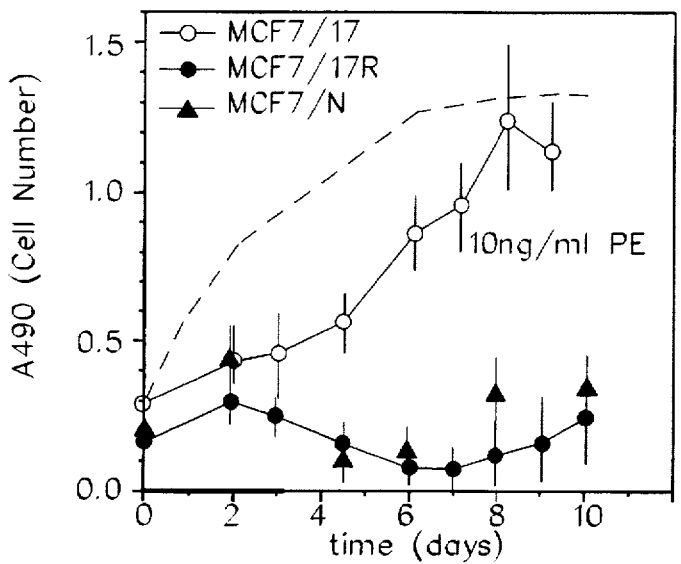
Figure 2F:
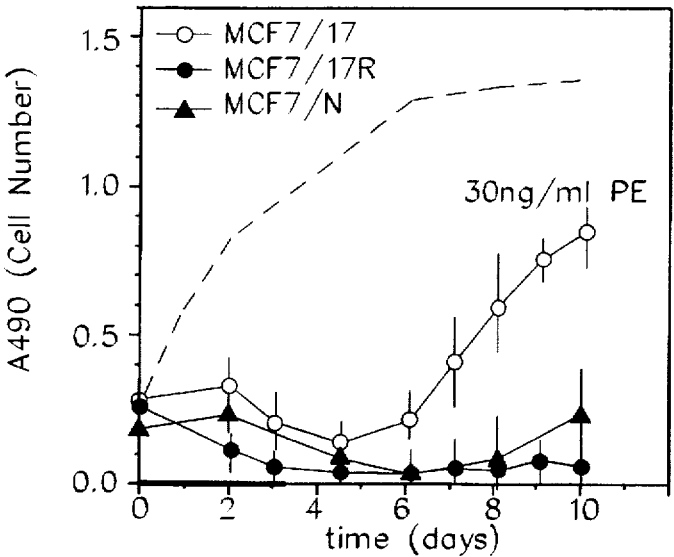

FIGS. 2D–F show time course experiments in which tranfectants containing antisense CAS undergo growth arrest upon toxin treatment but recover after removal of toxin Cell viability was determined by MTS assays in 96-well plates where A490 is proportional to the number of cells in each sample. MCF-7/17 cells, producing CAS antisense, showed growth about equal to that of the control cells, but a longer lag-phase before resuming growth after trypsinization. In FIG. 2E and 2F, a typical growth curve of cells without toxin (representing the mean of three experiments) is indicated by a broken line and the duration of toxin exposure is indicated by a bar on the X-axis.

EXAMPLE 3

CELLS MADE RESISTANT TO TOXIN-INDUCED APOPTOSIS BY ANTISENSE CAS EXPRESSION STILL HAVE TOXIN-ALTERED ELONGATION FACTOR-2 (EF2)

The results shown in FIG. 2C indicated that PE altered EF2 in the treated cells whether or not the CAS gene was present or transcribed in the sense or antisense orientation. This was directly confirmed using an ADP-ribosylation assay.

Extracts for assaying ADP-ribosylation of EF2 by PE were prepared by suspending PBS-washed cell pellets in lysis buffer (10 mM Tris, 10 mM KCl, 1.5 mM Mg-acetate, 6 mM mercaptoethanol, pH 7.5) for 30 min at 20° C. followed by homogenization. Then 0.2 vol 1.25M sucrose was added, the suspension was centrifuged (30 min, 4° C., 100,000×g) and the supernatant was dialyzed against lysis buffer containing 0.25M sucrose. Equal amounts of protein in extracts were incubated in 250 µl (final vol, adjusted with 50 mM Tris, 1 mM EDTA) assay buffer containing 40 mM DTT, with 1.5 µl $^{14}$C-NAD (Amersham, 287 mCi/µMole, 260 µCi/ml) and 10 ng/ml PE (final conc.) for 30 min at 37° C. Protein-associated radioactivity was precipitated with 12% TCA, and then washed with 6% TCA. The pellet was solubilized with 0.1M NaOH, neutralized with HCl and radioactivity was determined by counting disintegrations per min in scintillation liquid.

As shown in FIG. 2C, there was no difference in the incorporation of $^3$H-leucine between MCF-7 cells containing CAS antisense and the control cell lines, even though the MTS assay showed that the toxin sensitivity was very different between these cell lines. In these experiments, an additional control cell line which contained CAS expressed in the sense direction (called MCF-7/R) was included; it showed identical results as the experimental cells for $^3$H-leucine incorporation after PE treatment.

The direct measurement of the ability of PE to ADP-ribosylate EF2 in extracts of CAS antisense MCF-7/17 cells and in control cells shows that the sensitivity of EF2 in the toxin resistant transfectant was indistinguishable from controls (see Table 1). Thus, CAS antisense does not make cellular EF2 resistant to PE. The EF2 becomes modified as effectively in cells containing CAS antisense as in control cells.

TABLE 1

The immediate actions of PE and TNF are not affected in CAS antisense containing cells (PE).

| | | McF-7, McF-7/N (control) | McF-7/17 (CAS antisense) |
|---|---|---|---|
| PE | ADP-ribosylation activity (cpm) | 1328 ± 250 | 1329 ± 200 |
| | protein synthesis inhibition ($IC_{50}$) | 0.5–1 ng/ml | 0.5–1 ng/ml |
| | cell death ($LC_{50}$) | 1–2 ng/ml | 15–20 ng/ml |
| TNF | receptors/cell affinity | 17000 ± 4000 102 pM ± 8   pM | 17000 ± 5000 104 pM ± 17   pM |
| | cell death ($LC_{50}$) TNF alpha | 0.15 ng/ml | 1–3 ng/ml |
| | cell death ($LC_{50}$) TNF beta | 1–3 ng/ml | 20–30 ng/ml |

ADP-ribosylation of EF2 in cell extract was assayed as described above. Inhibition of protein synthesis was measured by incorporation of $^3$H-leucine 15 hrs after toxin exposure, and cell death was assessed by MTS assays (see FIG. 2). The $IC_{50}$ is the toxin concentration that reduces protein synthesis by 50% compared to untreated cells and $LC_{50}$ is the concentration that kills 50% of the cells (as measured in MTS assays). The number of TNF receptors per cell and affinity was determined by $^{125}$I-TNF alpha (Amersham) competition and displacement assays using the program "Ligand" for data processing (Munson, P. J., and Rodbard, D., *Meth. Enzymol.* 92: 543–576, 1983). The mean of those experiments ± S.E. is shown; within this error range, displacement assays gave slightly lower apparent receptor number and higher affinity than the mean and competition assays lower affinity and higher receptor numbers.

Thus, the mechanism by which the cells containing CAS antisense become resistant is "downstream" of the primary damage done to the cells by the toxin.

Figure 3:
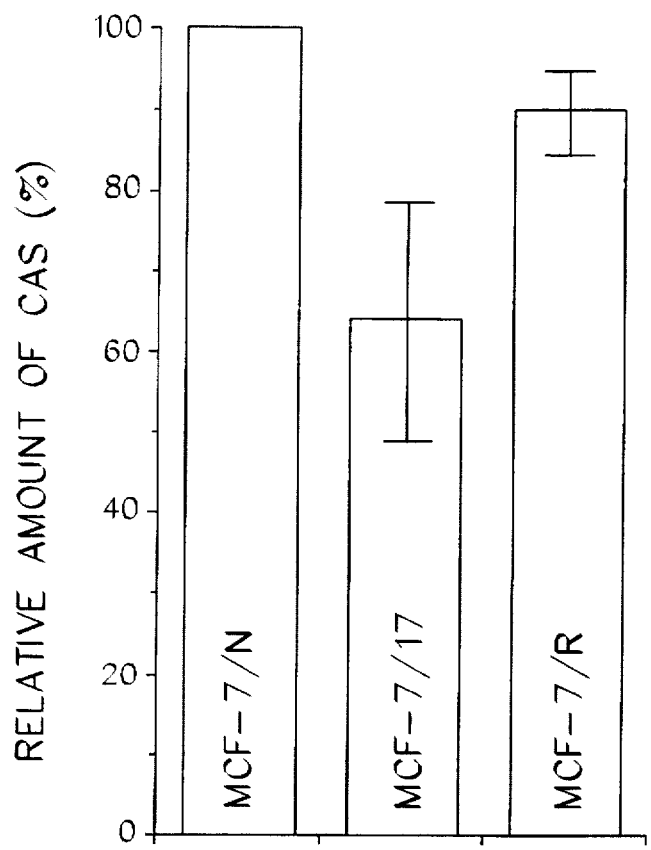
FIG. 3 shows that the relative amount of CAS protein detected in MCF-7 cells containing the CAS antisense clone (MCF-7/17) was reduced compared to that detected in MCF-7 cells containing the CAS sense clone (MCF-7/R) and control MCF-7 cells without a CAS clone (MCF-7/N).

One explanation for the observed protective effects of the CAS antisense plasmid on cells is interference with expression of the corresponding cellular gene. To evaluate this possibility, we examined the levels of CAS protein in MCF-7 cells containing the CAS antisense clone (pCDM/HE17; labeled MCF-7/17 on FIG. 3); containing the CAS sense clone (pCDM/HE17R; labeled MCF-7/R on FIG. 3) and control cells without a CAS clone (labeled MCF-7/N on FIG. 3). Using standard Western immunoblotting techniques (Sambrook, J., et al., *Molecular cloning. A Laboratory Manual.*, 2nd ed., 1989) and CAS-specific polyclonal antibodies (see Example 13 for details on antibody preparation), we found equal amounts of a CAS protein (of expected size about 100 kDa) in MCF-7/N and MCF-7/R cells, and reduced amounts in MCF-7/17 cells. FIG. 3 shows that CAS protein in cells containing the CAS antisense clone was detected in reduced amounts equal to about 65%±15% of that detected in the control MCF-7 cells. This result shows that the presense of CAS antisense reduces the intracellular levels of the CAS gene product.

EXAMPLE 4

GROWTH OF TOXIN TREATED CELLS MADE RESISTANT TO TOXIN-INDUCED APOPTOSIS BY ANTISENSE CAS EXPRESSION

To gain more information about the status of the cells that are resistant to PE, time course experiments were carried out at two concentrations of PE (10 and 30 ng/ml). These concentrations were chosen because they had maximal inhibitory effect on the growth of control cells (see FIG. 2A) and maximally inhibited protein synthesis (see FIG. 2C). In addition, cells containing sense plasmids as well as other controls were included. FIG. 2D–2F show the time course of treatment with PE. The MCF-7/17 cells containing CAS antisense were treated with 10 ng/ml of PE for three days (see FIG. 2E) and showed little or no growth compared to untreated cells (compare to FIG. 2D). However, when the PE was removed the cells began to grow and by day 8 reached almost the same cell number as the control cells that were not treated with PE. FIG. 2F shows that MCF-7/17 cells that were treated with 30 ng/ml of PE for 3 days showed no growth, but after removal of PE, recovered and resumed growth. In contrast, MCF-7/N cells, which contained only the pMC1neo/polyA plasmid, and MCF-7/17R cells which contained the pMC1neo/polyA plasmid and the pCDM/HE17R plasmid (CAS sense), showed no growth in the presence of 10 or 30 ng/ml of PE and did not recover after toxin removal (FIGS. 2E and 2F). This phenotype was also observed with the other control cell lines plasmids MCF-7/C and MCF-7/C2-C5.

These results show that cells containing the CAS antisense plasmid remain alive and begin to proliferate when the toxin is removed, in contrast to control cells which die as a consequence of toxin treatment. The results also show that the effect of the antisense plasmid is specific because cells containing the sense plasmid (MCF-7/17R), as well as other control plasmids, did not recover after toxin removal.

The morphology of cells exposed to toxins reflects the changes observed using the MTS and $^3$H-leucine incorporation assays. Cells were exposed to PE and TNF and the morphology of the cells was observed by phase contrast microscopy of a random field (at 250×magnification) after incubation with PE (10 ng/ml) or TNF alpha (1 ng/ml) for 3 days. Control cells (MCF-7/N) become rounded, refractile and detach from the plate surface indicating cellular death. The MCF-7/17 cells transfected with the CAS antisense plasmid remained attached to the plate surface.

The morphologic appearance of MCF-7/N cells and MCF-7/17 cells (containing the antisense plasmid) was observed without toxin treatment and after treatment with 10 ng/ml of PE for two days. The untreated cells grew as flattened cells in islands characteristic of MCF-7 cells. There was no obvious morphological difference between the MCF-7/N cells and MCF-7/17 cells. However, the appearance of the cells treated with 10 ng/ml of PE for two days was very different. No MCF-7/N cells were detected attached to the dish; all the cells were floating, refractile and many were disintegrating. In contrast, most of the MCF-7/17 cells remained flattened and attached to the dish and resembled cells that had not been treated with PE. This morphology occurred under conditions where the cells' ability to incorporate $^3$H-leucine into protein was arrested to background levels (see FIG. 2C at 10 ng/ml PE). This normal morphology was consistent with the cells' ability to resume growth when the toxin was removed (see FIG. 2E and 2F).

EXAMPLE 5

DNA DEGRADATION IS DECREASED IN CELLS MADE RESISTANT TO TOXIN-INDUCED APOPTOSIS BY ANTISENSE CAS EXPRESSION

Some cells undergo apoptosis upon exposure to ADP-ribosylating toxins (Kochi, S. K., and Collier, R. J., *Exp. Cell Res.* 208: 296–302, 1993; Chang, M. P., et al., *J. Biol. Chem.* 264: 15261–15267, 1989; Morimoto, H., and Bonavida, B., *J. Immunol.* 149: 2089–2094, 1992) Because MCF-7 cells containing the CAS antisense plasmid become less sensitive to ADP-ribosylating toxins without changing their susceptibility to toxin-mediated protein synthesis inhibition, it is likely that the CAS antisense affects the susceptibility of cells to undergo apoptosis. One hallmark of apoptosis is DNA degradation and the formation of a DNA ladder due to internucleosomal cleavage of chromosomal DNA (Compton, M. M., *Cancer Metast. Rev.* 11: 105–119, 1992). Therefore, cells treated with PE were used as a source of DNA (from the medium and soluble cell fraction) which was analyzed as described by Kochi and Collier (*Exp. Cell Res.* 208: 296–302, 1993). Nuclear DNA degradation is characteristic of apoptotic cells. Release of DNA fragments into cell culture supernatant was analyzed by labeling cells for 20 hrs with $^3$H-thymidine (Amersham), then changing the medium and exposing cells to toxin as described (Kochi, S. K., and Collier, R. J., *Exp. Cell Res.* 208: 296–302, 1993). DNA release was assayed by measuring radioactivity in the medium and in the soluble fraction of cells and comparing that to the total radioactivity.

Figure 4:
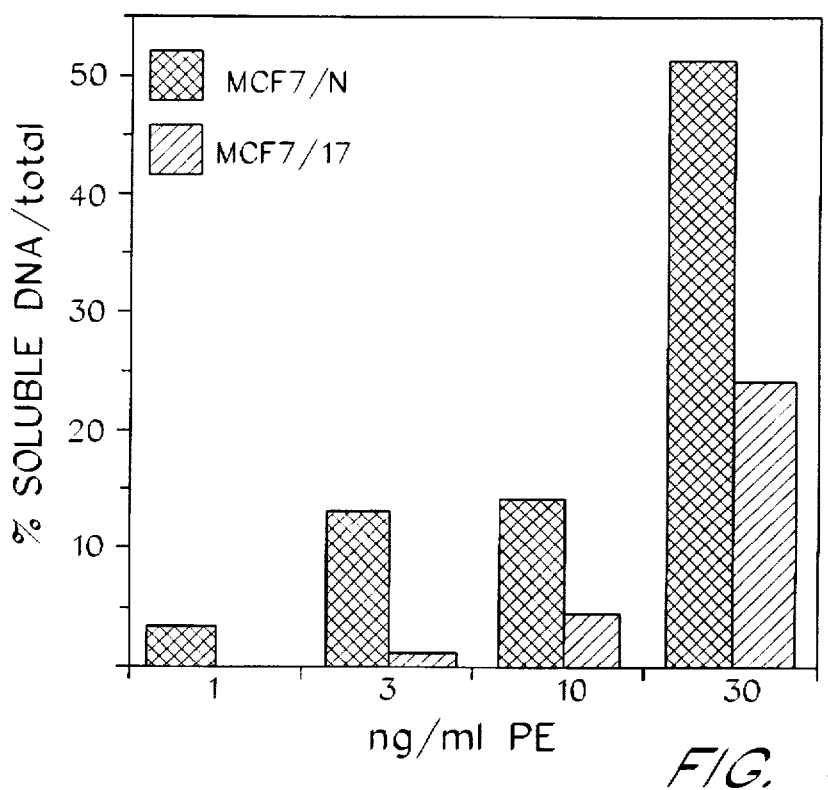
FIG. 4 shows that CAS antisense renders MCF-7 cells less susceptible to apoptosis as determined by degradation of chromosomal DNA which was assayed by release of $^3$H-containing DNA.

FIG. 4 shows that CAS antisense renders MCF-7 cells less susceptible to apoptosis as determined by nuclear DNA degradation. Toxin treatment induced degradation of chromosomal DNA as determined by two assays: radioactive measurement of degraded DNA present in the culture medium and visualization of the degraded DNA following gel separation.

To quantitate DNA degradation; $10^6$ cells were labeled with $^3$H-thymidine (1 mCi/ml) overnight and then treated with various amounts of PE for 15 hrs. The amount of $^3$H-thymidine in chromosomal DNA, the cellular soluble fraction and the medium was determined by scintillation counting as described (Kochi, S. K., and Collier, R. J., *Exp. Cell Res.* 208: 296–302, 1993).

As shown in FIG. 4, with increasing concentrations of PE, there is a concomitant increase in DNA released into the medium and into the soluble fraction of cells. Because intact genomic DNA is usually not present in the culture medium and the soluble cell fraction of healthy cells, this indicates extensive DNA degradation upon toxin treatment of control cells. In contrast, in MCF-7/17 cells containing CAS antisense, the production of soluble DNA was greatly diminished at all PE concentrations tested (shown in FIG. 4).

The nature of the soluble DNA was determined by isolating DNA from the medium, which contained most of the soluble DNA, and subjecting it to electrophoresis and autoradiography to detect the sizes of soluble DNA (i.e., to detect a "ladder" characteristic of internucleosomal DNA degradation). When analyzing internucleosomal DNA degradation we found that DNA of cells still attached to culture dishes was in most cases a smear (50000–200 bp) and the ladder fragments were difficult to visualize. However, DNA obtained from cell culture fluid by phenol/chloroform extraction and ethanol precipitation clearly showed a ladder. Therefore, DNA obtained from the medium was used to determine the extent of nuclear degradation and the sizes of the degraded DNA fragments. $^3$H-labeled DNA was isolated from the medium by phenol extraction and ethanol precipitation and separated by electrophoresis on a 1.5% agarose gel which was used to produce an autoradiograph.

The PE treated MCF-7/N cells displayed a typical nucleosomal ladder having wide bands of about 150–225 bp, about 300–425 bp, about 450–600 bp and in additional steps up to about 1500 bp. In contrast, the MCF-7/17 cells showed mostly higher molecular weight fragments (greater than 1500 bp) and a very faint DNA ladder of similar sizes as seen in the MCF-7/N cells but that was so faint it could not be photographically reproduced. Our finding that DNA degradation and nucleosomal ladder formation is diminished in MCF-7/17 cells containing CAS antisense suggests that toxin resistance is due to interference with an apoptosis pathway.

EXAMPLE 6

EXPRESSION OF ANTISENSE CAS MAKES CELLS LESS SUSCEPTIBLE TO APOPTOSIS INDUCED BY TUMOR NECROSIS FACTORS ALPHA AND BETA

It is well established that apoptosis can be induced in certain cell lines by TNF alpha and TNF beta. The toxins PE and DT produce cell death by causing inhibition of protein synthesis by modification of EF2, whereas TNF acts by receptor a different mechanism involving binding and signal transduction (Smith, C. A., et al., Cell 76: 959–962, 1994). Although two different mechanisms cause cell death, it has been suggested that DT-mediated and TNF-mediated cytotoxicity might share a common pathway leading to cell death (Morimoto, H., and Bonavida, B., J. Immunol. 149: 2089–2094, 1992). Thus, if this pathway were part of the apoptosis machinery, one might expect that cells that are resistant to PE-induced apoptosis might also be more resistant to TNF-induced apoptosis.

TNF binding was first demonstrated to show that MCF-7 cells express TNF receptors. Binding assays were performed essentially as previously described (Webber, K. O., et al., Mol. Immunol. in press, 1995). 3×10$^5$ cells per dish in 24-well plates were chilled and blocked with RPMI/5% BSA/50 mM BES/50 mM BES pH 7 for 1 hr at 4° C. and washed twice with binding buffer (RPMI/1% BSA/50 mM BES, pH7). $^{125}$I-labeled TNF alpha and cold TNF in binding buffer were then added and incubated for 2 hrs. For competition experiments, 80 pM final conc. of $^{125}$I-TNF, 12 nCi, 16 fmol/well (Amersham) was mixed with varying concentrations of unlabeled TNF. For Scatchard experiments serial dilutions, 18 to 70 pM, of labeled TNF were used. Labeled TNF was then removed and the cells were washed twice with binding buffer. Cell bound radioactivity was recovered in 0.5% SDS in TE and determined in a Beckman 5500B gamma counter. Receptor numbers and affinity was calculated using the LIGAND program (Munson, P. J., and Rodbard, D., Meth. Enzymol. 92: 543–576, 1983). Table 1 and FIG. 5 show that MCF-7 cells have TNF receptors and are sensitive to TNF mediated apoptosis.

Figure 5A:
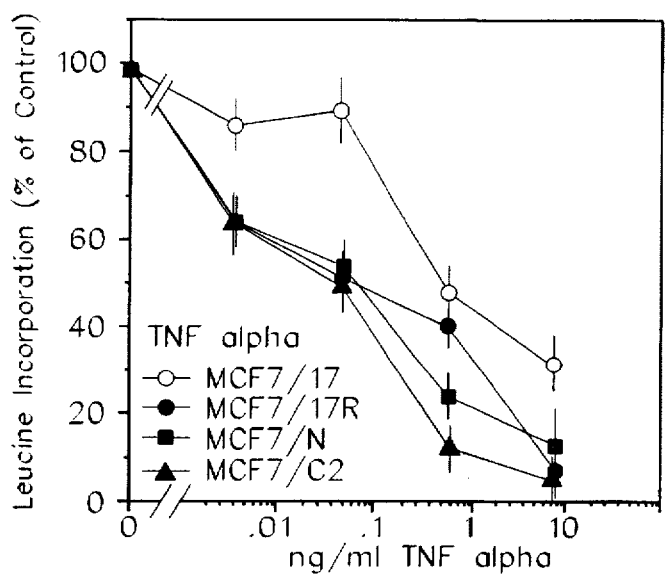
FIGS. 5A–5F shows that CAS antisense reduces the sensitivity of MCF-7 cells to TNF as determined by: $^3$H-leucine incorporation into cells treated with TNF alpha (FIG. 5A and 5E) and TNF beta (FIG. 5C); by cell growth over 9 days after treatment with TNF alpha (FIG. 5D) and TNF beta (FIG. 5E); and by TNF alpha receptor binding (FIG. 5F).
Figure 5B:
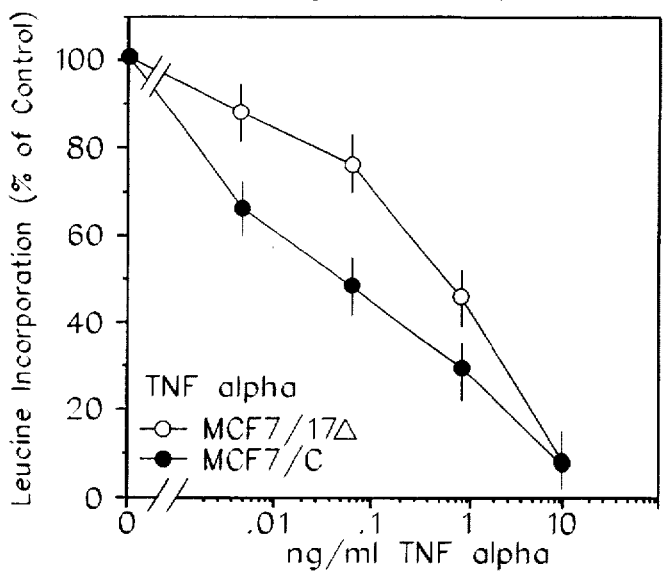
Figure 5C:
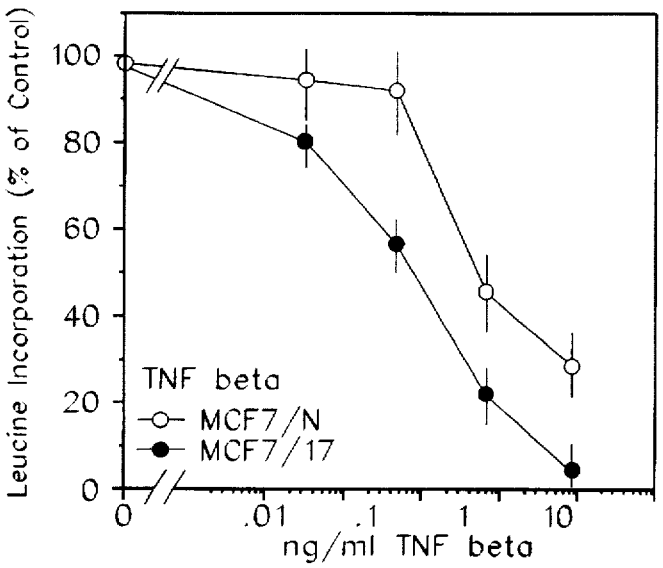
Figure 5D:
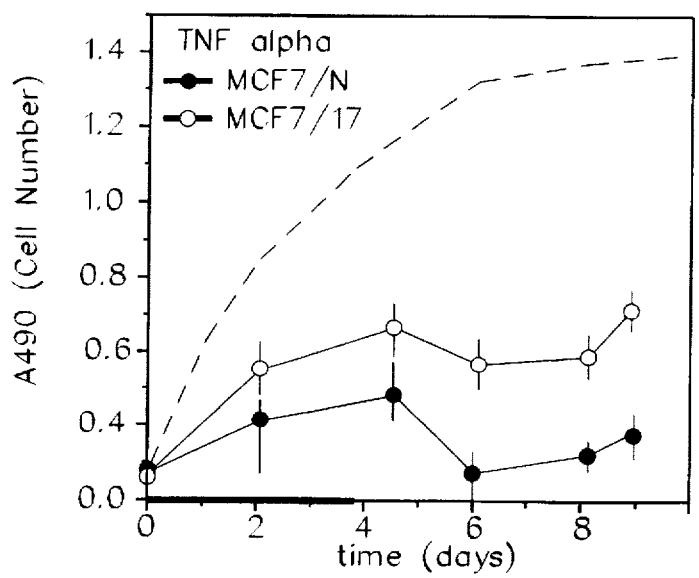
Figure 5E:
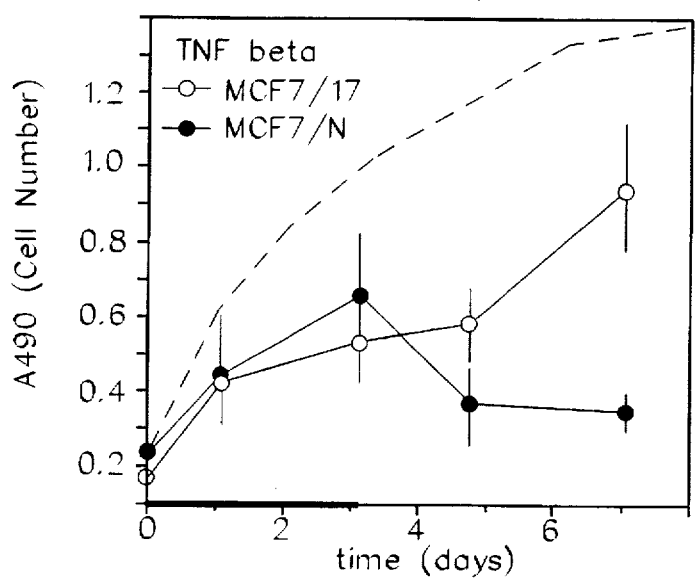

The effects of CAS antisense plasmids on TNF induced apoptosis in MCF-7 cells was then determined. $^3$H-leucine incorporation assays were used to quantitate killing by TNF. The assays were performed 3 days after TNF alpha (FIG. 5A and 5B) and TNF beta (FIG. 5C). FIG. 5 shows that CAS antisense reduces the sensitivity of MCF-7 cells to TNF. The IC$_{50}$ of TNF alpha on untransfected MCF-7 cells and cells containing control plasmids was approximately 0.1–0.2 ng/ml (FIG. 5A and 5B). The IC$_{50}$ of TNF beta was 2–3 ng/ml for the control (FIG. 5C). In contrast, MCF-7/17 cells bearing the CAS antisense plasmid were about 5–10-fold less sensitive to both TNF alpha (IC$_{50}$ about 1 ng/ml) and to TNF beta (IC$_{50}$ about 20 ng/ml) (FIG. 5A–5C).

This difference in TNF sensitivity between control cells and CAS antisense cells was also seen by examining the morphological appearance of TNF treated cells under phase contrast microscopy. Control cells treated with 1 ng/ml TNF were detached from the dishes and were disintegrating, while CAS antisense cells stayed attached to the dishes and resembled untreated cells. This phenotype was very similar to the effects seen with PE treated cells as described in Example 4.

Time course experiments were used to determine cell viability by MTS assays in 96 well plates as described in Examples 1 and 2. Similar to the phenotype of CAS antisense transfected MCF-7 cells that were treated with PE, TNF treatment of these cells produced growth inhibition, which was reversed after TNF removal (see FIG. 5D for TNF alpha and FIG. 5E for TNF beta, and compare to FIGS. 2D–F). An average growth curve (mean of three experiments) of cells without toxin is indicated by a broken line and the duration of TNF exposure is indicated by a bar on the X-axis. MCF-7/17 and MCF-7/17Δ contain CAS antisense. Controls were MCF-7/17R that contains the sense plasmid, MCF-7/C that contains the pCDM8 library vector without insert, and MCF-7/C2 that contains a randomly chosen library plasmid with an unknown insert (see FIG. 1B for comparison). The control cells did not survive TNF treatment and did not recover after TNF removal.

Figure 5F:
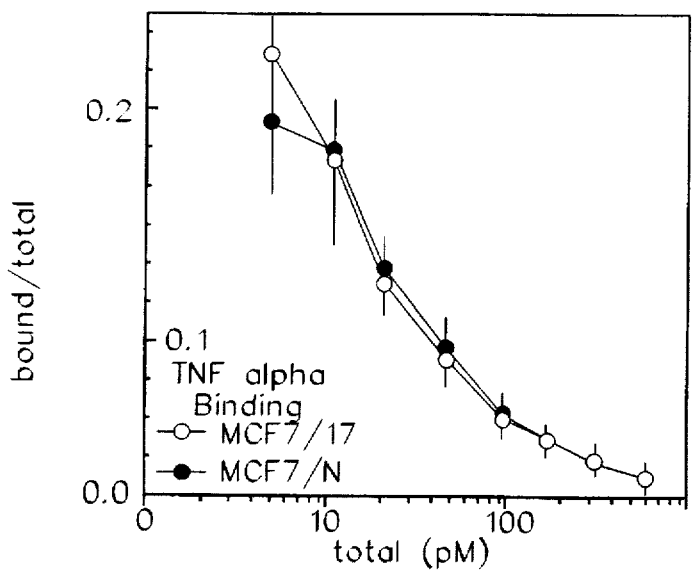

The altered sensitivity of cells to TNF when the CAS antisense plasmid was present was not due to interference with the immediate action of TNF, which is binding to its receptor. FIG. 5F and Table 1 show that the TNF receptor numbers and affinity remained unchanged in MCF-7/17 cells containing CAS antisense.

EXAMPLE 7

THE DNA SEQUENCE OF A COMPLETE CAS cDNA REVEALS HOMOLOGY TO THE YEAST CHROMOSOME SEGREGATION GENE CSEI

The CAS antisense plasmid that reduces the sensitivity of cells to PE, DT and TNF contained only a 436 bp fragment of a CAS cDNA. To obtain a complete (normal human) CAS coding sequence, we used the cDNA insert of pCDM/HE17Δ as a probe to screen a human placenta cDNA library in lambda gt11.

1×10⁶ plaques of a Lambda gt11 cDNA library from placenta polyA RNA (Clontech™) were screened by hybridization with a radioactivity labeled cDNA insert of pCDM/HE17Δ using standard techniques (Sambrook, J., et al., *Molecular cloning. A Laboratory Manual.*, 2nd ed., 1989). The largest inserts, about 2.4 kb, included the 3'-end but not the 5'-end of the cDNA with an estimated size of 3.2 kb.

Although several cDNA inserts were isolated, the longest being about 2.4 kb, no full length clone was obtained. A full length clone was expected to be about 3.2 kb from the mRNA size in Northern blots (discussed in detail in Example 8 and shown in FIG. 7). This size was also expected if the CAS cDNA were about the same size as the yeast CSE1 cDNA.

Because all of the isolated clones were from the 3' end of the cDNA, the 5' end of the cDNA was obtained by the RACE method (Apte and Siebert, *Biotechniques* 15: 890–93, 1993; Frohman et al., *Proc. Natl. Acad. Sci. USA* 85: 8998–9002, 1988) using 5'-RACE-Ready™ placenta cDNA (Clontech) as template and the Clontech anchor primer 5'-CTGGTTCGGCCCACCTCTGAA GGTTCCAGAATCGATAG-3' (SEQ ID NO:3) and a CAS specific primer 5'-TAATGAGGTCTCTCACAAA-3' (SEQ ID NO:4) positioned 160 bp downstream of the 5' end of the longest lambda insert. Amplification was done for 30 cycles (2 min at 94° C., 2 min at 60° C., 2 min at 72° C. and a final extension of 10 min at 72° C.) using a Perkin Elmer GeneAmp XL™ PCR kit. A single 1160 bp fragment was obtained which was the correct 5' end of the CAS because the overlap of this fragment 3' end matched with the first 160 bp of the longest previously obtained lambda clone 5' end. The lambda fragments and RACE fragments were cloned into pCRII (Invitrogen) and sequenced with an ABI™ 373A sequencer and ABI Dyedeoxy Terminator™ kit.

The nucleotide sequence and deduced amino acid sequence of CAS are shown in FIG. 6. The CAS cDNA from HeLa used as a screening probe had the same sequence as the human placenta cDNA and corresponds to nucleotides 2100–2536 of the full-length clone. The coding regions of human CAS and yeast CSE1 (Xiao, Z., et al., *Mol. Cell. Biol.* 13: 4691–4702, 1993) are of approximately the same size, 974 and 960 amino acids respectively, and their sequence is similar. The deduced translation products have approximately the same size and are homologous. The overall homology (protein similarity) is 59% and in some portions, the homology is greater than 75% with 50% identity. For example, CAS protein sequence showed identity with the CSE1 protein sequence over amino acid stretches of 9 amino acids (in one region), 8 amino acids (in one region) and 7 amino acids (in three regions). No defined protein other than CSE1 showed significant homology to CAS. However, some previously sequenced but functionally undefined short "EST" sequences of between 209 and 346 bp were found to have homology or to match identically to the 5' or 3' end of CAS cDNA. There was no significant protein sequence motif in the CAS sequence that would indicate its molecular function.

EXAMPLE 8

EXPRESSION OF CAS IN NORMAL HUMAN TISSUES AND HUMAN CANCER CELL LINES

The homology illustrated in FIG. 6B indicates that the CAS gene is conserved relative to the yeast CSE1 gene and therefore is likely to have a similar important cellular function. For comparison, the yeast CSE1 is an essential gene involved in cell division (i.e., homozygous CSE1 mutations are lethal; Xiao, Z., et al., *Mol. Cell. Biol.* 13: 4691–4702, 1993). However, the function of the human CAS gene in the process of apoptosis, as defined by the results in Examples 1–6, differs from that described for the CSE1 gene in yeast.

To determine if CAS may have a role in cell proliferation as well as apoptosis, the expression of CAS in human tissues and in tumor cell lines was analyzed by Northern blotting (Sambrook, J., et al., *Molecular cloning. A Laboratory Manual.*, 2nd ed. 1989). Northern blots containing about 2 μg polyA mRNA of various tissues separated on a denaturing formaldehyde 1.2% agarose gel (Clontech) were hybridized with radioactive labeled ($^{32}$P random primed, about 10⁹ cpm/μg) CAS probe (insert of pCDM/HE17Δ) or actin and/or GAPDH control probes (Clontech) having comparable specific activities for 20 hrs at 50° C. in Hybrisol 1™ (50% Formamide, Oncor) solution. Blots were exposed to Kodak XAR2™ film (–70° C. with screen) for 18–20 hrs (to detect CAS) or about 6 hr (to detect actin and GAPDH), and then scanned on a Molecular Dynamics Phosphoimager 425™. RNA levels were quantitated by comparing the signals of CAS to the actin and/or GAPDH signals.

The control hybridizations showed that approximately equal amounts of RNA were loaded for most tissues except for skeletal muscle which could not be exactly quantitated due to additional actin band and apparently elevated GAPDH. Some tissues were tested in duplicate to demonstrate the reproducibility of the results.

Figure 7:
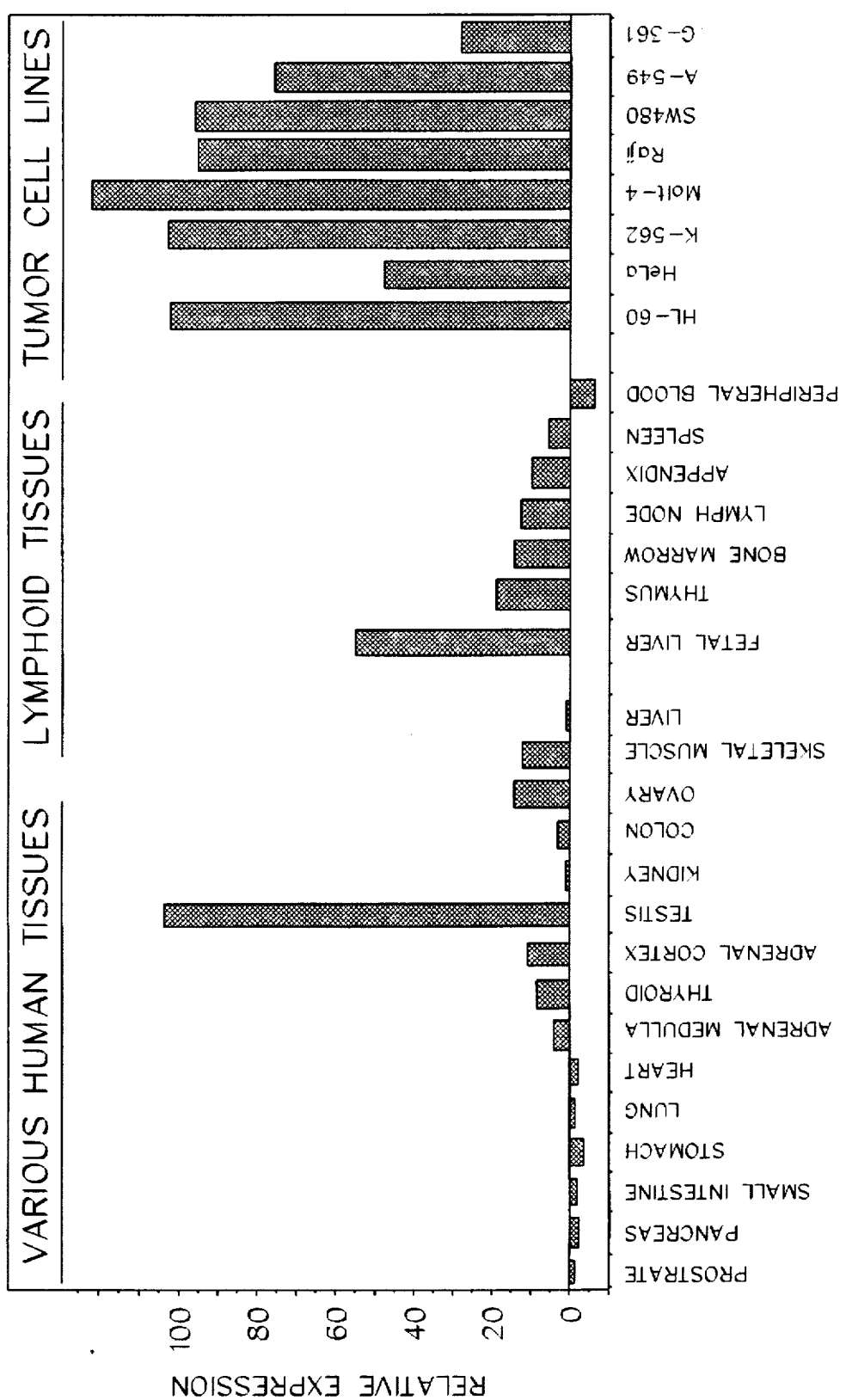
FIG. 7 shows the relative expression of CAS in human tissues and some cancer cell lines, as measured by Northern blots, from which the relative mRNA levels in tissues and tumor cell lines were determined.

The CAS mRNA, detected band of about 3 kb, was found in many tissues including pancreas, adrenal medulla, thyroid, adrenal cortex, testis, thymus, small intestine, stomach, spleen, lymph node, thymus, appendix, peripheral blood, bone marrow, fetal liver, spleen, prostate, ovary, small intestine, colon, heart, brain, placenta, lung, liver, skeletal muscle and kidney. A quantitation of CAS expression, normalized to the expression of actin or GAPDH is shown in FIG. 7. Relative mRNA levels in tissues and tumor cell lines were determined by comparing the CAS intensities with the mean of actin and GAPDH signals using a Molecular Dynamics Phosphoimager™. For determining "relative expression" the CAS/Control ratio found in most tissues (the mean of levels found in prostate, small intestine, colon, heart, brain, lung and pancreas) was defined as a "basal level" and were set to 1. Testis, which is the tissue having the highest expression level, was set to 100. The others were determined relative to these tissues.

Expression was very high in testis and fetal liver which contain many actively proliferating cells, and was elevated (above basal level) in tissues that contain some proliferating cells, e.g. lymphoid tissues. Expression was slightly elevated in skeletal muscle. Very low expression was detected in peripheral blood which does not contain proliferating cells.

In addition, various proliferating tumor cell lines, e.g. SW480 (colon), A549 (lung) and HL60, K562, Molt4 and Raji (leukemias and lymphomas) contained high levels of CAS mRNA.

Based on these results, expression of CAS can be used as a marker for cell proliferation. Because cell proliferation is a hallmark of cancer cells, detecting CAS expression in cells above basal levels can serve as a method for detecting cancer cells.

EXAMPLE 9

THE CAS GENE IS LOCATED IN THE 20q13 REGION OF HUMAN CHROMOSOME 20

To identify the chromosomal localization of the CAS gene, Southern blot hybridization of a CAS probe to a panel of somatic cell hybrids that represent the different human chromosomes in a mouse or hamster background was performed Under stringent conditions, a 436 bp cDNA fragment covering the CAS cDNA from position 2100 to 2536 (see FIG. 6A) was hybridized to the panel.

A southern blot containing human (male and female) genomic DNA cut with PstI, mouse and hamster DNA, and genomic DNA from somatic cell hybrids containing single human chromosomes was obtained from ONCOR and hybridized under stringent conditions with the CAS probe. On the autoradiograph, mouse and hamster lines were easily distinguished because under these stringent conditions, hybridization of CAS to mouse DNA was easily seen, but no hybridization was detected to hamster DNA. The CAS probe hybridized to human female and male DNA and to DNA from the mouse cell line that carries a human chromosome 20.

Two PstI fragments of human genomic DNA specifically hybridized with the CAS probe as expected because the probe contained an internal PstI site. Thus at least two fragments would be expected when genomic CAS DNA is cut with PstI. Of the different somatic cell hybrids containing one human chromosome each (in mouse or hamster cell background), these two fragments were detected in the cell line that contained human chromosome 20. Thus, based on these hybridization results, the CAS gene is located on chromosome 20.

To further map the CAS gene, the human CEPH YAC Megabase library (Centre d'Etude du Polymorphisme Humaine) was screened by PCR using the primers P1 (5'GACATCCCGTCTTCCTATATG) (SEQ ID NO:5) and P2 (5'AAGAAGCCTCACTAGAGCAGGA) (SEQ ID NO:6) which bound to and amplified a 90 bp fragment when CAS cDNA and human genomic DNA were individually used as templates. One YAC clone, YAC 953-b-4, was specifically amplified with these primers.

Microsatellite markers were identified on or near that YAC address using techniques well known in the art and this information was used to position the CAS gene relative to typed microsatellite markers in the YAC library. YAC 953-b-4 overlaps with YACs positive for the genetic marker D20S176, which is mapped to the long arm of human chromosome 20, indicating that the CAS gene is located within a 2-3 Mb region of the genetic marker D20S176 on chromosome 20. This position was confirmed by Fluorescent In Situ Hybridization (FISH) (Thompson, C. T. & Gray J. W., *J Cell. Biochem.* (Suppl.) 17G: 139–143, 1993) analysis using a P1 clone containing the human CAS gene (see Example below) as probe. This position is close to the 20q13 region that is amplified in certain breast tumors and breast cancer cell lines like HTB20. This region is known to contain amplifications that correlate with aggressive progression of breast cancer and probably harbors one or more oncogene(s) responsible for the aggressive cancer phenotype (Tanner M. M. et al., *Cancer Res.* 54, 4257–4260, 1994).

EXAMPLE 10

THE CAS GENE IS AMPLIFIED IN HUMAN CANCER CELL LINES

Because the CAS gene is located in a region known to undergo amplification in tumor cells, the amplification of the CAS gene was examined in a number of tumor cell lines using Southern blotting.

Quantitative Southern hybridizations were used to determine the relative number of copies of the CAS gene in tumor cell lines using techniques well known to those skilled in the art (Sambrook, J., et al., *Molecular cloning. A Laboratory Manual.*, 2nd ed., 1989). As shown in FIG. 8, the cell lines analyzed were BT-474 (also known as HTB20), MCF-7, LS174T, COLO205, SW-480 and N-87 (all of which are available from the American Type Culture Collection, Rockville, Md.). As an internal control, the actin gene was also hybridized to determine the normal gene copy number without amplification. This probe is an appropriate control also for cell lines which are described to be aneuploid, because chromosome 7, which harbors the actin gene, is over-represented in breast cancer cell lines (HTB20). Therefore, this control probe gives a very conservative estimate of CAS amplification (because it can already be elevated itself) and can compensate potential over-representation of chromosome 20 in aneuploid cell lines.

FIG. 8 shows the comparison of the ratio of the hybridization signals between control signal and CAS signal in different cell lines hybridized with the CAS probe and actin control probes The ratio between CAS and actin control signals was determined by quantitatively scanning the bound radioactivity on the Southern blots using a Phosphoimager™. Human genomic DNA was used as a reference for single copy status of CAS (the actin/CAS signal ratio was set to 1 for human genomic DNA).

Figure 8A:
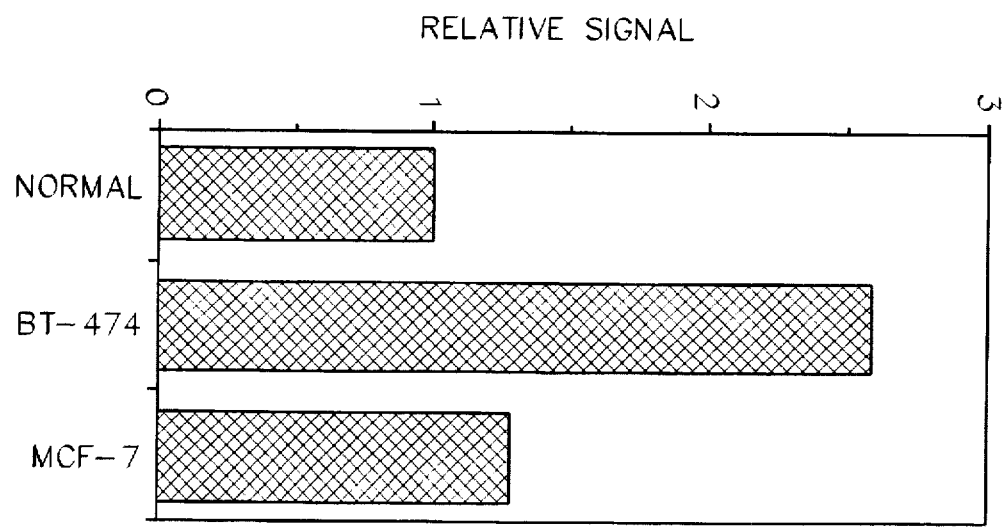
FIGS. 8A&B shows the copy number of the CAS gene detected in various cancer cell lines.
Figure 8B:
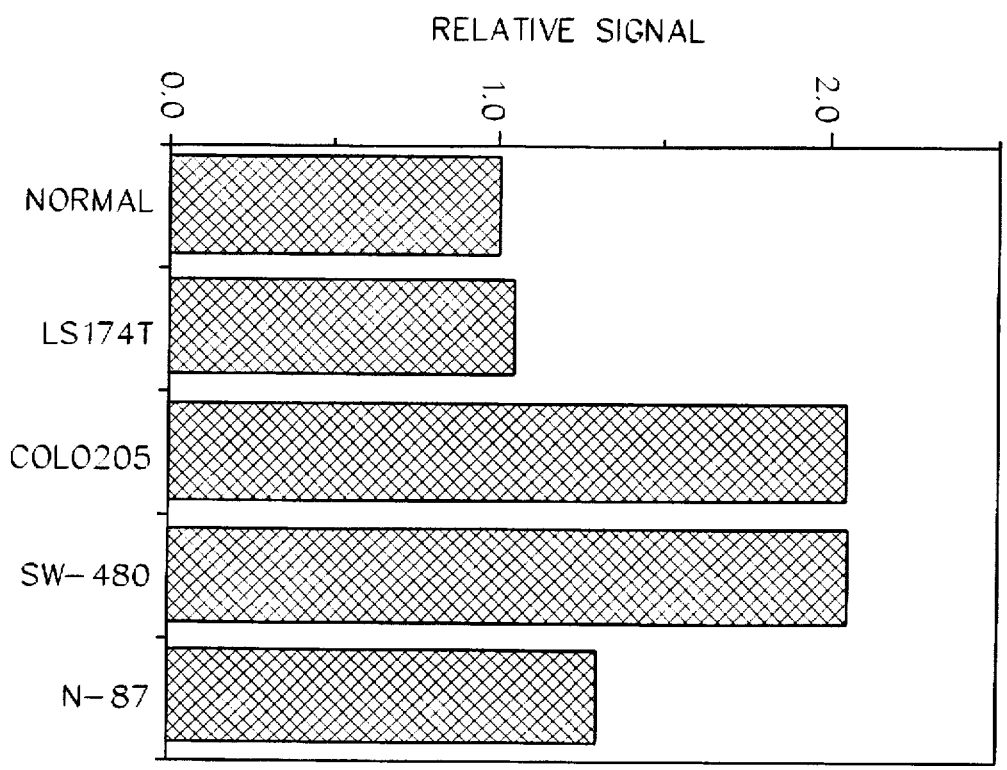

The ratio for normal human genomic DNA was set to 1 and the other samples are relative to that. If one assumes a linear relation between gene targets on the filter and hybridization signal, this ratio approximates the copy number of CAS. The results shown in FIG. 8 show that the CAS gene is amplified in the cell lines BT-474 (HTB20), COLO205 and SW-480 when compared to the normal human genomic DNA controls and to cancer cell lines MCF-7, LS174T and N-87. FIG. 8A shows the results for two breast cancer cell lines; FIG. 8B shows the results for colon cancer cell lines (SW480, COLO205, LS147T) and a gastric cancer (N87) cell line.

The CAS gene was amplified in the breast cancer cell line HTB20 which was previously described to contain a 20q13 amplification. In contrast, the CAS gene was not amplified in a cell line (MCF-7) that does not contain the described amplification.

Although a close link of CAS to the minimal amplification region in 20q13 can be established by the YAC localization (see Example 9), we cannot rule out that CAS is close to but not directly in the region that has been defined as the main amplification region. Furthermore, the 20q13 region that is found to be amplified in certain cancers and cell lines is not a homogenous region, but consists of different regions that lie close together and contain various degrees of (possibly independent) amplifications. For example, Tanner et al., (*Cancer Res.* 54, 4257–4260, 1994) defined one minimal high amplification region, but also noted surrounding regions being amplified to a lesser degree, and different amplifications in different breast cancer cell lines. Therefore, to gain more information about CAS amplification in certain cancers, we performed FISH analysis (Thompson, C. T. & Gray J. W., *J Cell. Biochem.* (Suppl.) 17G: 139–143, 1993) using the P1/hCAS clone (described in Example 11) on BT474 breast cancer cells. These cells showed CAS amplification in quantitative Southern hybridizations. We found by FISH analysis that CAS was amplified 74 fold (up to 14 copies per cell) in these cells and also that the CAS gene sequence was translocated from the 20q13 locus to various other unidentified chromosomal locations.

To analyze whether CAS is amplified in other cancer cell lines in addition to the than breast cancer line, we analyzed by Southern blot hybridization genomic DNA from three cell lines derived from colon cancer (COLO205, LS174T and SW480) and one gastric cancer cell line (N87). Again, human genomic DNA was used as a single copy CAS reference control. FIG. 8B shows that DNAs of the colon cancer cell lines SW480 and COLO205 had stronger CAS signals than human genomic DNA. The other cell lines showed approximately the same CAS signal. The quantitation of the Southern hybridization signals by Phosphoimager™ analysis indicated a 2-fold amplification of CAS DNA in the colon cancer cell lines COLO205 and SW480. Thus, CAS is amplified not only in cell lines of breast cancer but also in other types of cancer including two out of three colon cancer cell lines that were analyzed. FISH analysis showed that this amplification in color cancer cells was not due to specific amplification of CAS DNA alone. Instead, in these cells, the entire chromosome 20 or a larger portion of the chromosome (e.g., the 20q arm) was amplified.

Because CAS is like other known oncogenes related to apoptosis and cell proliferation, and it is amplified in cell lines of breast and other cancers, it is possible that CAS plays a role or is causative for cancer. Thus, the detection of CAS amplification (or other genomic/cDNA alternations involving CAS) may be of value and possibly a predictive factor in cancer diagnosis and therapy.

EXAMPLE 11

ISOLATION OF GENOMIC CLONE CONTAINING THE HUMAN CAS GENE

A P1-clone containing the CAS gene, called P1/hCAS, was isolated from a human genomic P1-library by standard molecular biology and PCR techniques as described by Sternberg (*Trends in Genetics* 8: 11–16, 1992). The PCR primers P1 comprising 5'GACATCCCGTCTTCCTATATG 3' (SEQ ID NO:5) and P2 comprising 5'AAGAAGCCT-CACTAGAGCAGGA 3' (SEQ ID NO:6) located in the human CAS cDNA, which amplify a 90 bp CAS-specific DNA fragment from human genomic DNA were used to identify a P1 clone from the P1-library of GENOME SYSTEMS that hybridized to these primers. This P1 clone was called P1/hCAS. Because the primers used bind specifically to the CAS gene DNA, the isolated P1-clone contains at least part of the human CAS gene.

Figure 9:
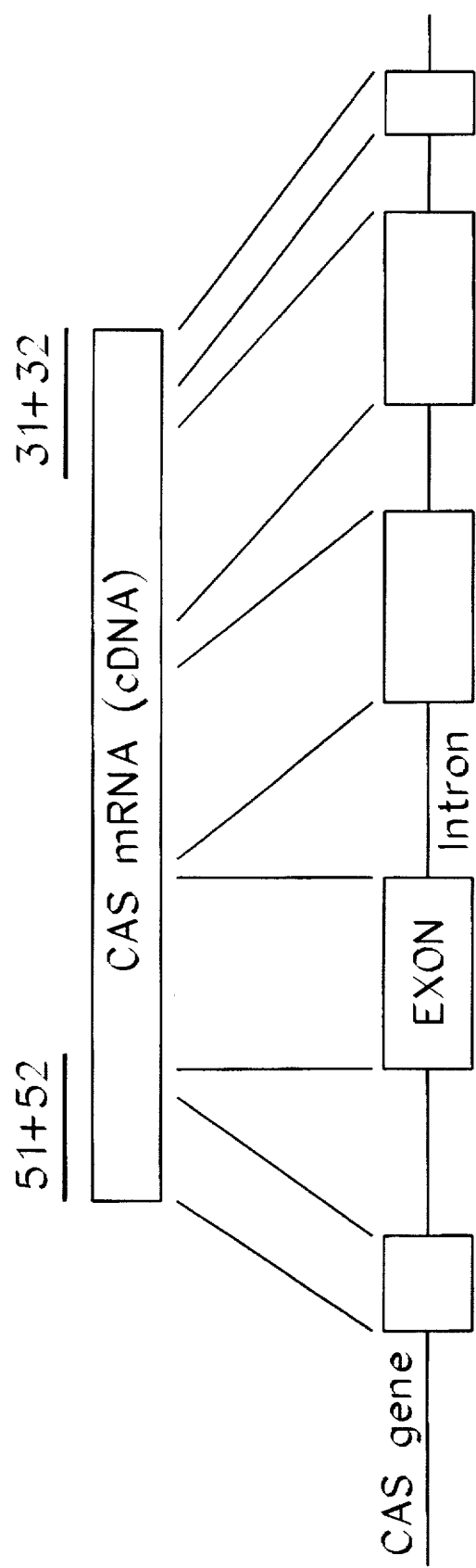
FIG. 9 shows a hypothetical, schematic organization of typical eukaryotic gene to represent the CAS gene and depict PCR amplification of genomic CAS DNA using the combinations of primers represented by the numbers 51+52 and 31+32.

The presence of the full length CAS gene in this P1 CAS clone was confirmed by PCR analysis of P1/hCAS using the primer pair P51 comprising 5'TGTGAAGCCGATC-GAGTGGC 3' (SEQ ID NO:7) and P52 comprising 5'TTCAGGGACATCCTGAAAGT 3' (SEQ ID NO:8) which amplify a 5'-end fragment from human CAS cDNA and P31 comprising 5'CCCCACTGATGGACACTGA 3' (SEQ ID NO:9) and P32 comprising 5'CTCACCAT-TGATGGAACCC 3' (SEQ ID NO:10) which amplify a 3'-end fragment from CAS cDNA (see FIG. 9 for a diagramatic representation of these primers and their location on a hypothetical CAS gene) The rationale of using these primers and PCR analysis of P1/hCAS to confirm the completeness of the gene is depicted in FIG. 9 which is a schematic diagram of the organization of typical eukaryotic genes and does not represent the actual arrangement of introns and exons in the CAS gene. P51 and P52 will amplify a DNA fragment from P1/hCAS only if the 5'-end of the gene is present. Similarly, P31 and P32 will only result in a PCR fragment if the gene portion containing the 3'-end of the CAS coding region is present. FIG. 9 shows these combinations of primers as bars above the box labelled "CAS mRNA (cDNA)".

Using this approach, a specific DNA fragment was obtained with the P51 and P521 primer combination in a PCR reaction when the P1/hCAS was used as the PCR template but not when the template was not included in the reaction. The DNA amplified using this combination of P51 and P52 primers was about 2000 bp long. The 3'-end was also present on the P1/hCAS clone because when the combination of primers P31 and P32 were used with the P1/hCAS clone as template a similar fragment was amplified by PCR, whereas no fragments was observed without the P1/hCAS template.

A comparison of the fragment sizes obtained from this (3'-end) PCR with the distance of the primers in the CAS cDNA indicated that the 3'-end fragment is significantly larger than the distance on the cDNA. Thus, it is likely that an intron is present in between these primer positions in the human CAS gene.

EXAMPLE 12

PCR DETECTION OF CAS GENOMIC DNA

Cancer cells often contain genetic abnormalities relative to normal cells that can be detected at the genomic level. To detect such genetic abnormalities associated with deletions, translocations or amplification of the 20q13 region, a PCR-based assay using primers specific for the CAS gene sequence is used.

Using the P51 and P52 combination of primers (P51/P52) genomic DNA from tissue suspected of having cancerous cells is amplified by PCR for a limited number of cycles. Similarly, the same source of genomic DNA is used as a template in a PCR reaction using the P31 and P32 combination (P31/P32) of primers (see also Example 11). As a control, genomic DNA from normal human tissue is similarly amplified in an independent reaction. The amplified DNA is then separated by gel electrophoresis, stained with a DNA intercalating dye, and the relative amount of DNA in each sample is determined by the degree of fluorescence of the amplified DNA under UV light. The amount of fluorescence in the amplification product from normal genomic DNA serves as a baseline control representing unamplified CAS sequences. In tissue in which the DNA containing the CAS gene is deleted (e.g., on one of the two chromosomes 20), a lesser amount of amplified CAS DNA is detected. In tissue in which the DNA containing the CAS gene is amplified, a greater amount of amplified CAS DNA is detected. In tissue in which the CAS gene has been translocated to another location, a lesser (or no) CAS gene amplification may be detected depending on the location of the translocation breakpoint, or fragments of different lengths may be obtained following PCR amplification.

For performing this PCR-based assay, the following methods are used. Genomic DNA is purified from human tissues suspected of containing cancerous cells and from normal tissue as a control using standard purification methods. All PCR reactions are done in a final volume of 50 µl containing 250 ng of genomic DNA, 25 pmol of each primer (either the P31/P32 or the P51/P52 combination), 50 mM KCl, 10 mM Tris-HCl (pH 8.8), 1.5 mM MgCl$_2$, 0.1% Triton X-100, 200 µM of each dNTP and 2.5 units of TaqI DNA polymerase. Amplification is for 15 cycles each consisting of 5 sec at 92° C., 1 min at 65° C. and 4 min at 72° C. followed by a single cycle of 12 min at 72° C. After amplification, 20 µl of each reaction is applied to an agarose gel for electrophoretic separation and staining using standard methods (Sambrook, J., et al., *Molecular cloning. A Laboratory Manual.*, 2nd ed., 1989).

Using this procedure, DNA isolated from tissue taken from a breast tumor is examined and found to contain more CAS genetic material compared to DNA from normal breast tissue for both the P31/P32 and P51/P52 combinations of primers. Thus, amplification of the CAS gene is detected in the tumor tissue.

It will be appreciated by those skilled in the art that a kit including the P31/P32 and/or P51/P52 combinations of primers or other primers specific for PCR amplification of CAS gene sequences could be used to detect genetic amplification of the CAS sequence. Determination of appropriate combinations of primers is well known in the art and is easily done using the sequence provided in SEQ ID NO:1. Such PCR-based kits are useful for detection in vitro or in vivo of cancer cells in human tissues. In addition to the CAS-specific primers, such a PCR kit may include primers specific for other areas of the genome (particularly for Chromosome 20 sequences) reagents used in performing the PCR (including but not limited to water, salts, buffers, dNTP solutions, TaqI DNA polymerase or other heat-resistant DNA polymerases). The amplified DNA sequence could be detected by separation and visualization of the products using gel electrophoresis or by other methods well known to those skilled in the art including DNA hybridization, filter binding and other well known techniques for specifically detecting specific DNA molecules.

Furthermore, it will be appreciated by those skilled in the art that a PCR-based kit may also be used to detect increased expression of the CAS gene. For example, a kit that includes a primer for transcribing CAS mRNA into cDNA by use of a reverse transcriptase (or other enzymes capable of producing cDNA) and primer combinations for then PCR amplifying the cDNA so produced would detect increased CAS gene expression. The amplified DNA may be detected using any of the procedures discussed above or other DNA detection methods well known in the art.

Thus, kits for detection of CAS genetic material or expression of CAS genes would include the PCR primer combinations needed for amplification and one or more reagents for performing PCR. A PCR kit may also reagents for detecting the amplified DNA.

EXAMPLE 13

PRODUCTION OF ANTIBODIES THAT SPECIFICALLY RECOGNIZE CAS PROTEIN

To raise antibodies against the human CAS protein, we constructed plasmids for expression of fragments of CAS protein as recombinant His-tagged proteins in *E. coli* containing either amino acids 1–284 or 327–669 of CAS. Clone C46 contains CAS amino acids 327–669 and clone C2.6 contains CAS amino acids 1–284. Recombinant CAS fragments were produced in *E. coli* cells containing these plasmids and purified from solubilized inclusion bodies by Ni-affinity chromatography (on Quiagen Ni-Chelation resin). After separation by SDS gel electrophoresis and Coomassie blue staining, only a single band of purified protein was detected for each of the clones corresponding to amino acids 1–284 or 327–669 of the CAS protein.

Rabbits were immunized with these purified proteins and polyclonal antibodies were produced that detected CAS protein on Western blots of total cell extracts from MCF-7 cells and W138 cells or from *E. coli* cells containing the recombinant CAS fragments. In all cases, only a single band was detected using anti-CAS antibodies produced against the CAS amino acids 1–284 when the serum was diluted either 1:000 or 1:2000 in appropriate buffer. Control Western blots using the same amount of antigen and serum from pre-immunization rabbits at a 1:1000 dilution showed no detectable CAS band. Anti-CAS antibodies against CAS amino acids 327–669 showed a single band of detected protein on a Western blot when the serum was used at a 1:1000 dilution, and a weak band was detected when the serum was used at a 1:2000 dilution. Control serum (at a dilution of 1:1000 or 1:2000) from the same rabbit before immunization showed no detectable signal on the Western blot.

Antibodies were purified from the anti-CAS sera by affinity chromatography with immobilized CAS fragments using standard techniques. The same fragments that were used for immunization were immobilized on BioRad Affigel and affinity purification was performed using methods well known to those skilled in the art.

When affinity purified anti-CAS antibodies against CAS amino acids 327–669 were used at a 1:2000 dilution on a Western blot, a strong single band of CAS protein was detected showing that the purification concentrated the antibodies relative to the serum which barely detected CAS when diluted 1:2000. The affinity purified anti-CAS antibodies were used for immunohistological analysis of CAS expression in cells and tumors and for fluorescence activated cell sorter (FACS) analyses presented below.

EXAMPLE 14

ANTI-CAS ANTIBODIES CAN DISTINGUISH RESTING (NORMAL) CELLS FROM PROLIFERATING AND TUMOR CELLS

Because we have shown that CAS mRNA is highly expressed in proliferating cells and tumor cell lines, it is feasible to assume, that also the CAS protein should be present at high levels in proliferating and tumor cells and at low levels in normal cells (with few exceptions, e.g. testis). Because of that, the detection of relative amounts of CAS protein can be of value for tumor diagnosis, e.g. to distinguish tumor tissues from normal tissues.

Figure 10:
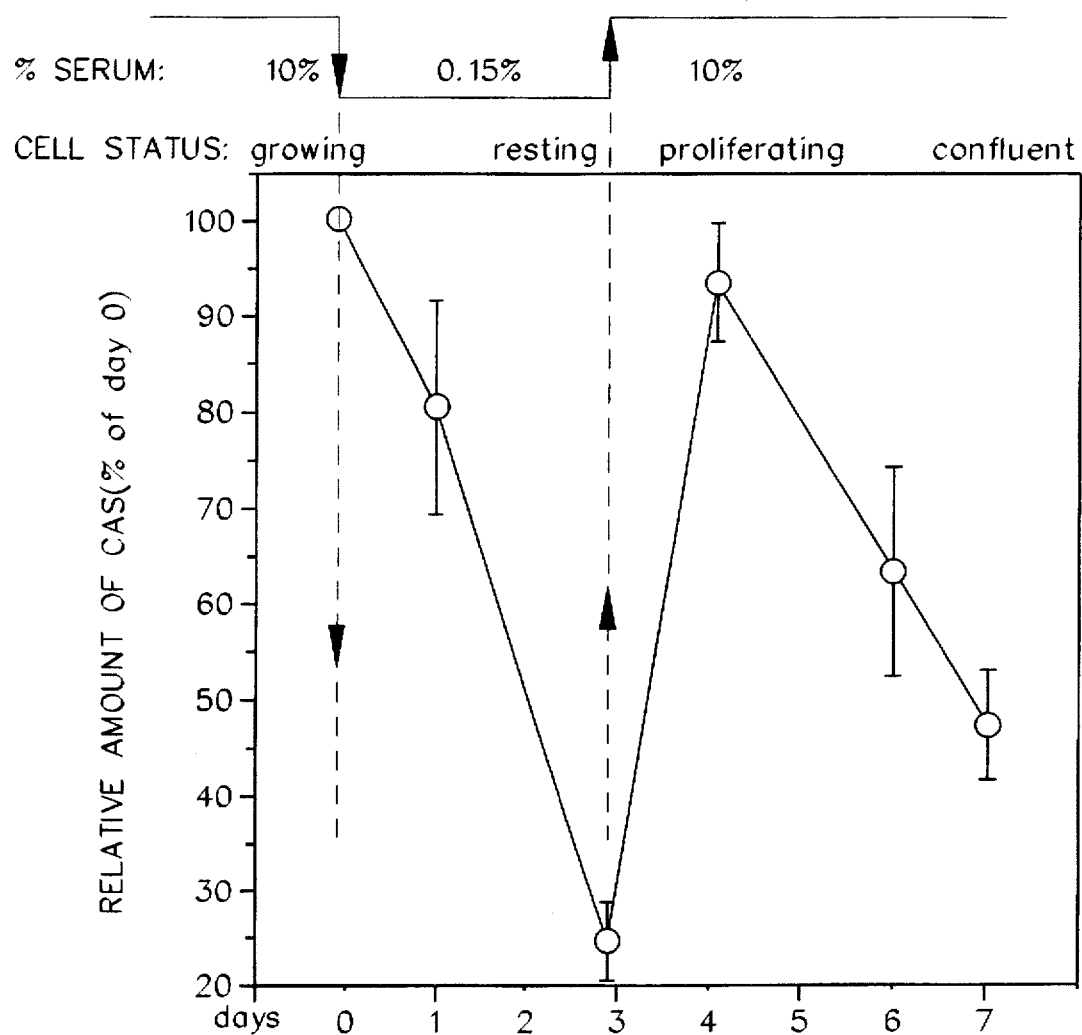
FIG. 10 shows the relative amount of CAS protein detected in growing and resting human WI38 fibroblasts.

To demonstrate that the CAS protein level in cells is dependant on their proliferation status, we analyzed the CAS content in total cell extracts of resting human W138 fibroblasts (maintained in serum depleted medium) and of actively growing W138 cells (grown in medium containing 15% serum). The CAS protein was detected as a single protein band of about 100 kDa by Western blotting of total cellular protein using anti-CAS antibodies (made as in Example 13). FIG. 10 shows that CAS was expressed at a higher level in growing cells and at significantly lower levels in resting cells. Thus, detection of elevated CAS expression in cells is indicative of cell proliferation.

To analyze whether CAS protein levels are elevated in growing cancer cells relative to normal cells, we compared the CAS protein content in total cell extracts of human W138 fibroblasts (resting and actively growing, see above) with the CAS content in MCF-7 breast cancer cells, again using Western blots with anti-CAS antibodies. We found that CAS was expressed at a significantly higher level in the cancer cells compared to the "normal" cells, independent of whether the normal cells were growing or resting.

The high levels of CAS protein in cancer cells can also be detected using CAS-specific antibodies and secondary antibodies with fluorescent tags and immunofluorescence techniques well known to those skilled in the art. The presence of CAS protein in various cancer cells was detected by standard immunofluorescence and microscopic examination of MCF-7 breast cancer and A431 epidermoid cells. FACS analysis was used to detect CAS protein in CA46 lymphoma cells. When cells were stained with anti-CAS fluorescently labeled antibodies, the cells exhibited an average relative fluorescence about 100-fold greater than that of cells that were not stained with anti-CAS fluorescently labeled antibodies In this FACS analysis, the relative fluorescence resulting from binding of the fluorescently-labeled anti-CAS antibody (on the Y axis) was graphed as a function of the DNA content of the cells determined by propidium iodite staining (on the X axis).

It will be appreciated by those skilled in the art that a kit for diagnosing cancer can be based on anti-CAS antibodies such as those described above. An antibody based diagnostic kit could use the anti-CAS antibodies in a variety of ways to detect cellular CAS protein in cancer cells. A kit could be used to detect binding of anti-CAS antibodies to CAS protein by directly measuring fluorescence from anti-CAS antibodies directly labeled with a fluorescent marking in a fluorescence immunoassay using techniques well known to those skilled in the art. Alternatively, a kit could rely on other ways of detecting binding of anti-CAS antibody to CAS protein including detection of fluorescence using a fluorescently-labeled secondary antibody to bind to the anti-CAS antibody (based on specific binding to the anti-CAS antibody or cross-species antibody binding, dependent on either the variable or constant regions of the anti-CAS antibody, respectively). It will be appreciated by those skilled in the art that radiolabeling of the anti-CAS antibody or the secondary antibody that binds to the anti-CAS antibody could be effectively substituted for fluorescent labeling and the kit would rely on a radioimmunoassay (RIA). Furthermore, an enzyme substrate attached to the anti-CAS antibody or the secondary antibody that binds to the anti-CAS antibody could be used to detect binding by measuring the relative enzymatic activity of the bound antibodies in a enzyme linked immunosorbent assay (ELISA) using reactions well known to those skilled in the art. Those skilled in the art will further appreciate that an antibody-based kit could use latex beads, either directly linked to the anti-CAS antibody or linked to the secondary antibody that binds to the anti-CAS antibody. Anti-CAS antibodies could further be used in a kit in which the anti-CAS antibodies serve as part of a sandwich immunoassay in which the CAS protein is immobilized to a solid support for detection. It will be understood that these examples are nonlimiting and additional methods of antibody-based detection of CAS protein are also contemplated for use in a kit of the present invention.

We conclude that elevated CAS expression in cells is indicative for cell proliferation, and that higher levels of CAS protein are detectable in cancer cells, compared to most normal cells.

The relevant portions of all the articles cited herein are incorporated by reference.

While particular embodiments of the invention have been described in detail, it will be apparent to those skilled in the art that these embodiments are exemplary rather than limiting, and the true scope of the invention is defined by the claims that follow.

We claim:

1. A purified and isolated cDNA coding for a human CAS protein and consisting of the nucleotide sequence of SEQ ID NO:1.

2. A purified and isolated cDNA coding for a portion of a human CAS protein and consisting of nucleotides 2100 to 2536 of SEQ ID NO:1.

3. A method of detecting human cancerous cells, comprising measuring expression of a human CAS gene in a cell sample and detecting human CAS gene expression at a level at least two-fold greater than expression of a human CAS gene in normal noncancerous human cells.

4. The method of claim 3, wherein CAS gene expression is measured by detecting the level of CAS mRNA in cells.

5. The method of claim 4, wherein said CAS mRNA is detected by hybridization with a complementary DNA.

6. The method of claim 4, wherein said CAS mRNA is detected by a polymerase chain reaction.

7. A method of detecting human cancer cells in a biological sample, comprising the steps of:

obtaining a biological sample which comprises human cells;

measuring the number of copies of a human CAS gene present in said cells; and comparing the measured number of copies with the number of copies of said human CAS gene in normal noncancer cells, wherein said number of copies of a CAS gene is at least two-fold greater in human cancer cells than the number of copies of a CAS gene in normal human noncancer cells.

8. The method of claim 7, wherein the number of copies of a CAS gene is measured by detecting the amount of hybridization of a DNA complementary to SEQ ID NO:1, wherein said complementary DNA is a CAS gene.

9. The method of claim 7, further comprising measuring the number of copies of a gene which is known to present as a single copy gene in both cancerous and normal noncancerous cells and comparing the number of copies of the single copy gene to the number of copies of a CAS gene in both cancerous and normal noncancerous cells.

10. The method of claim 9, wherein the single copy gene is an actin gene.

11. The method of claim 7, wherein the number of copies of a CAS gene is determined by a polymerase chain reaction that amplifies either a 5' portion of the CAS gene, a 3' portion of the CAS gene, or both a 5' and a 3' portion of the CAS gene.

12. The method of claim 7, wherein the cancer cells are breast tissue cells.

13. The method of claim 7, wherein the cancer cells are colon cells.

14. A purified and isolated antisense CAS DNA consisting of nucleotides 2100 to 2536 of SEQ ID NO:1.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3180 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
GTCGCGCCAT TTTGCCGGGG TTTGAATGTG AGGCGGAGCG GCGGCAGGAG CGGATAGTGC      60

CAGCTACGGT CCGCGGCTGG GGTTCCCTCC TCCGTTTCTG TATCCCCACG AGATCCTATA     120

GCAATGGAAC TCAGCGATGC AAATCTGCAA ACACTAACAG AATATTTAAA GAAAACACTT     180

GATCCTGATC CTGCCATCCG ACGTCCAGCT GAGAAATTTC TTGAATCTGT TGAAGGAAAT     240

CAGAATTATC CACTGTTGCT TTTGACATTA CTGGAGAAGT CCCAGGATAA TGTTATCAAA     300

GTATGTGCTT CAGTAACATT CAAAAACTAT ATTAAAAGGA ACTGGAGAAT TGTTGAAGAT     360

GAACCAAACA AAATTTGTGA AGCCGATCGA GTGGCCATTA AAGCCAACAT AGTGCACTTG     420

ATGCTTAGCA GCCCAGAGCA AATTCAGAAG CAGTTAAGTG ATGCAATTAG CATTATTGGC     480

AGAGAAGATT TTCCACAGAA ATGGCCTGAC TTGCTGACAG AAATGGTGAA TCGCTTTCAG     540
```

```
AGTGGAGATT  TCCATGTTAT  TAATGGAGTC  CTCCGTACAG  CACATTCATT  ATTTAAAAGA   600
TACCGTCATG  AATTTAAGTC  AAACGAGTTA  TGGACTGAAA  TTAAGCTTGT  TCTGGATGCC   660
TTTGCTTTGC  CTTGACTAA   TCTTTTTAAG  GCCACTATTG  AACTCTGCAG  TACCCATGCA   720
AATGATGCCT  CTGCCCTGAG  GATTCTGTTT  TCTTCCCTGA  TCCTGATCTC  AAAATTGTTC   780
TATAGTTTAA  ACTTTCAGGA  TCTCCCTGAA  TTTGGGAAG   GTAATATGGA  AACTTGGATG   840
AATAATTTCC  ATACTCTCTT  AACATTGGAT  AATAAGCTTT  TACAAACTGA  TGATGAAGAG   900
GAAGCCGGCT  TATTGGAGCT  CTTAAAATCC  CAGATTTGTG  ATAATGCCGC  ACTCTATGCA   960
CAAAAGTACG  ATGAAGAATT  CCAGCGATAC  CTGCCTCGTT  TTGTTACAGC  CATCTGGAAT  1020
TTACTAGTTA  CAACGGGTCA  AGAGGTTAAA  TATGATTTGT  TGGTAAGTAA  TGCAATTCAA  1080
TTTCTGGCTT  CAGTTTGTGA  GAGACCTCAT  TATAAGAATC  TATTTGAGGA  CCAGAACACG  1140
CTGACAAGTA  TCTGTGAAAA  GGTTATTGTG  CCTAACATGG  AATTTAGAGC  TGCTGATGAA  1200
GAAGCATTTG  AAGATAATTC  TGAGGAGTAC  ATAAGGAGAG  ATTTGGAAGG  ATCTGATATT  1260
GATACTAGAC  GCAGGGCTGC  TTGTGATCTG  GTACGAGGAT  TATGCAAGTT  TTTTGAGGGA  1320
CCTGTGACAG  GAATCTTCTC  TGGTTATGTT  AATTCCATGC  TGCAGGAATA  CGCAAAAAAT  1380
CCATCTGTCA  ACTGGAAACA  CAAAGATGCA  GCCATCTACC  TAGTGACATC  TTTGGCATCA  1440
AAAGCCCAAA  CACAGAAGCA  TGGAATTACA  CAAGCAAATG  AACTTGTAAA  CCTAACTGAG  1500
TTCTTTGTGA  ATCACATCCT  CCCTGATTTA  AAATCAGCTA  ATGTGAATGA  ATTTCCTGTC  1560
CTTAAAGCTG  ACGGTATCAA  ATATATTATG  ATTTTTAGAA  ATCAAGTGCC  AAAAGAACAT  1620
CTTTTAGTCT  CGATTCCTCT  CTTGATTAAT  CATCTTCAAG  CTGGAAGTAT  TGTTGTTCAT  1680
ACTTACGCAG  CTCATGCTCT  TGAACGGCTC  TTTACTATGC  GAGGGCCTAA  CAATGCCACT  1740
CTCTTTACAG  CTGCAGAAAT  CGCACCGTTT  GTTGAGATTC  TGCTAACAAA  CCTTTTCAAA  1800
GCTCTCACAC  TTCCTGGCTC  TTCAGAAAAT  GAATATATTA  TGAAAGCTAT  CATGAGAAGT  1860
TTTTCTCTCC  TACAAGAAGC  CATAATCCCC  TACATCCCTA  CTCTCATCAC  TCAGCTTACA  1920
CAGAAGCTAT  TAGCTGTTAG  TAAGAACCCA  AGCAAACCTC  ACTTTAATCA  CTACATGTTT  1980
GAAGCAATAT  GTTTATCCAT  AAGAATAACT  TGCAAAGCTA  ACCCTGCTGC  TGTTGTAAAT  2040
TTTGAGGAGG  CTTTGTTTTT  GGTGTTACT   GAAATCTTAC  AAAATGATGT  GCAAGAATTT  2100
ATTCCATACG  TCTTTCAAGT  GATGTCTTTG  CTTCTGGAAA  CACACAAAAA  TGACATCCCG  2160
TCTTCCTATA  TGGCCTTATT  TCCTCATCTC  CTTCAGCCAG  TGCTTTGGGA  AAGAACAGGA  2220
AATATTCCTG  CTCTAGTGAG  GCTTCTTCAA  GCATTCTTAG  AACGCGGTTC  AAACACAATA  2280
GCAAGTGCTG  CAGCTGACAA  AATTCCTGGG  TTACTAGGTG  TCTTTCAGAA  GCTGATTGCA  2340
TCCAAAGCAA  ATGACCACCA  AGGTTTTTAT  CTTCTAAACA  GTATAATAGA  GCACATGCCT  2400
CCTGAATCAG  TTGACCAATA  TAGGAAACAA  ATCTTCATTC  TGCTATTCCA  GAGACTTCAG  2460
AATTCCAAAA  CAACCAAGTT  TATCAAGAGT  TTTTTAGTCT  TTATTAATTT  GTATTGCATA  2520
AAATATGGGG  CACTAGCACT  ACAAGAAATA  TTTGATGGTA  TACAACCAAA  AATGTTTGGA  2580
ATGGTTTTGG  AAAAAATTAT  TATTCCTGAA  ATTCAGAAGG  TATCTGGAAA  TGTAGAGAAA  2640
AAGATCTGTG  CGGTTGGCAT  AACCAACTTA  CTAACAGAAT  GTCCCCCAAT  GATGGACACT  2700
GAGTATACCA  AACTGTGGAC  TCCATTATTA  CAGTCTTTGA  TTGGTCTTTT  TGAGTTACCC  2760
GAAGATGATA  CCATTCCTGA  TGAGGAACAT  TTTATTGACA  TAGAAGATAC  ACCAGGATAT  2820
CAGACTGCCT  TCTCACAGTT  GGCATTTGCT  GGGAAAAAAG  AGCATGATCC  TGTAGGTCAA  2880
ATGGTGAATA  ACCCCAAAAT  TCACCTGGCA  CAGTCACTTC  ACATGTTGTC  TACCGCCTGT  2940
```

```
CCAGGAAGGG TTCCATCAAT GGTGAGCACC AGCCTGAATG CAGAAGCGCT CCAGTATCTC    3000

CAAGGGTACC TTCAGGCAGC CAGTGTGACA CTGCTTTAAA CTGCATTTTT CTAATGGGCT    3060

AAACCCAGAT GGTTTCCTAG GAAATCACAG GCTTCTGAGC ACAGCTGCAT TAAAACAAAG    3120

GAAGTTTTCC TTTTGAACTT GTCACGAAAA AAAAAAAAAA AAAAAAAAAA AAAAAAAAA    3180
```

( 2 ) INFORMATION FOR SEQ ID NO:2:

( i ) SEQUENCE CHARACTERISTICS:
    ( A ) LENGTH: 971 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Met Glu Leu Ser Asp Ala Asn Leu Gln Thr Leu Thr Glu Tyr Leu Lys
 1               5                  10                  15

Lys Thr Leu Asp Pro Asp Pro Ala Ile Arg Arg Pro Ala Glu Lys Phe
            20                  25                  30

Leu Glu Ser Val Glu Gly Asn Gln Asn Tyr Pro Leu Leu Leu Leu Thr
        35                  40                  45

Leu Leu Glu Lys Ser Gln Asp Asn Val Ile Lys Val Cys Ala Ser Val
    50                  55                  60

Thr Phe Lys Asn Tyr Ile Lys Arg Asn Trp Arg Ile Val Glu Asp Glu
65                  70                  75                  80

Pro Asn Lys Ile Cys Glu Ala Asp Arg Val Ala Ile Lys Ala Asn Ile
                85                  90                  95

Val His Leu Met Leu Ser Ser Pro Glu Gln Ile Gln Lys Gln Leu Ser
            100                 105                 110

Asp Ala Ile Ser Ile Ile Gly Arg Glu Asp Phe Pro Gln Lys Trp Pro
        115                 120                 125

Asp Leu Leu Thr Glu Met Val Asn Arg Phe Gln Ser Gly Asp Phe His
    130                 135                 140

Val Ile Asn Gly Val Leu Arg Thr Ala His Ser Leu Phe Lys Arg Tyr
145                 150                 155                 160

Arg His Glu Phe Lys Ser Asn Glu Leu Trp Thr Glu Ile Lys Leu Val
                165                 170                 175

Leu Asp Ala Phe Ala Leu Pro Leu Thr Asn Leu Phe Lys Ala Thr Ile
            180                 185                 190

Glu Leu Cys Ser Thr His Ala Asn Asp Ala Ser Ala Leu Arg Ile Leu
        195                 200                 205

Phe Ser Ser Leu Ile Leu Ile Ser Lys Leu Phe Tyr Ser Leu Asn Phe
    210                 215                 220

Gln Asp Leu Pro Glu Phe Trp Glu Gly Asn Met Glu Thr Trp Met Asn
225                 230                 235                 240

Asn Phe His Thr Leu Leu Thr Leu Asp Asn Lys Leu Leu Gln Thr Asp
                245                 250                 255

Asp Glu Glu Glu Ala Gly Leu Leu Glu Leu Leu Lys Ser Gln Ile Cys
            260                 265                 270
```

```
Asp Asn Ala Ala Leu Tyr Ala Gln Lys Tyr Asp Glu Glu Phe Gln Arg
        275                 280                 285

Tyr Leu Pro Arg Phe Val Thr Ala Ile Trp Asn Leu Leu Val Thr Thr
    290                 295                 300

Gly Gln Glu Val Lys Tyr Asp Leu Leu Val Ser Asn Ala Ile Gln Phe
305                     310                 315                 320

Leu Ala Ser Val Cys Glu Arg Pro His Tyr Lys Asn Leu Phe Glu Asp
                325                 330                 335

Gln Asn Thr Leu Thr Ser Ile Cys Glu Lys Val Ile Val Pro Asn Met
            340                 345                 350

Glu Phe Arg Ala Ala Asp Glu Ala Phe Glu Asp Asn Ser Glu Glu
        355                 360                 365

Tyr Ile Arg Arg Asp Leu Glu Gly Ser Asp Ile Asp Thr Arg Arg Arg
    370                 375                 380

Ala Ala Cys Asp Leu Val Arg Gly Leu Cys Lys Phe Phe Glu Gly Pro
385                     390                 395                 400

Val Thr Gly Ile Phe Ser Gly Tyr Val Asn Ser Met Leu Gln Glu Tyr
                405                 410                 415

Ala Lys Asn Pro Ser Val Asn Trp Lys His Lys Asp Ala Ala Ile Tyr
            420                 425                 430

Leu Val Thr Ser Leu Ala Ser Lys Ala Gln Thr Gln Lys His Gly Ile
        435                 440                 445

Thr Gln Ala Asn Glu Leu Val Asn Leu Thr Glu Phe Phe Val Asn His
    450                 455                 460

Ile Leu Pro Asp Leu Lys Ser Ala Asn Val Asn Glu Phe Pro Val Leu
465                     470                 475                 480

Lys Ala Asp Gly Ile Lys Tyr Ile Met Ile Phe Arg Asn Gln Val Pro
                485                 490                 495

Lys Glu His Leu Leu Val Ser Ile Pro Leu Leu Ile Asn His Leu Gln
            500                 505                 510

Ala Gly Ser Ile Val Val His Thr Tyr Ala Ala His Ala Leu Glu Arg
        515                 520                 525

Leu Phe Thr Met Arg Gly Pro Asn Asn Ala Thr Leu Phe Thr Ala Ala
    530                 535                 540

Glu Ile Ala Pro Phe Val Glu Ile Leu Leu Thr Asn Leu Phe Lys Ala
545                     550                 555                 560

Leu Thr Leu Pro Gly Ser Ser Glu Asn Glu Tyr Ile Met Lys Ala Ile
                565                 570                 575

Met Arg Ser Phe Ser Leu Leu Gln Glu Ala Ile Ile Pro Tyr Ile Pro
            580                 585                 590

Thr Leu Ile Thr Gln Leu Thr Gln Lys Leu Leu Ala Val Ser Lys Asn
        595                 600                 605

Pro Ser Lys Pro His Phe Asn His Tyr Met Phe Glu Ala Ile Cys Leu
    610                 615                 620

Ser Ile Arg Ile Thr Cys Lys Ala Asn Pro Ala Ala Val Val Asn Phe
625                     630                 635                 640

Glu Glu Ala Leu Phe Leu Val Phe Thr Glu Ile Leu Gln Asn Asp Val
                645                 650                 655

Gln Glu Phe Ile Pro Tyr Val Phe Gln Val Met Ser Leu Leu Leu Glu
            660                 665                 670

Thr His Lys Asn Asp Ile Pro Ser Ser Tyr Met Ala Leu Phe Pro His
        675                 680                 685

Leu Leu Gln Pro Val Leu Trp Glu Arg Thr Gly Asn Ile Pro Ala Leu
```

-continued

```
                    690                           695                           700
Val  Arg  Leu  Leu  Gln  Ala  Phe  Leu  Glu  Arg  Gly  Ser  Asn  Thr  Ile  Ala
705                      710                           715                      720

Ser  Ala  Ala  Ala  Asp  Lys  Ile  Pro  Gly  Leu  Gly  Val  Phe  Gln  Lys
                         725                      730                      735

Leu  Ile  Ala  Ser  Lys  Ala  Asn  Asp  His  Gln  Gly  Phe  Tyr  Leu  Leu  Asn
                    740                      745                      750

Ser  Ile  Ile  Glu  His  Met  Pro  Pro  Glu  Ser  Val  Asp  Gln  Tyr  Arg  Lys
          755                           760                      765

Gln  Ile  Phe  Ile  Leu  Leu  Phe  Gln  Arg  Leu  Gln  Asn  Ser  Lys  Thr  Thr
     770                      775                           780

Lys  Phe  Ile  Lys  Ser  Phe  Leu  Val  Phe  Ile  Asn  Leu  Tyr  Cys  Ile  Lys
785                      790                           795                      800

Tyr  Gly  Ala  Leu  Ala  Leu  Gln  Glu  Ile  Phe  Asp  Gly  Ile  Gln  Pro  Lys
                    805                      810                           815

Met  Phe  Gly  Met  Val  Leu  Glu  Lys  Ile  Ile  Ile  Pro  Glu  Ile  Gln  Lys
               820                      825                      830

Val  Ser  Gly  Asn  Val  Glu  Lys  Lys  Ile  Cys  Ala  Val  Gly  Ile  Thr  Asn
          835                      840                      845

Leu  Leu  Thr  Glu  Cys  Pro  Pro  Met  Met  Asp  Thr  Glu  Tyr  Thr  Lys  Leu
     850                      855                      860

Trp  Thr  Pro  Leu  Leu  Gln  Ser  Leu  Ile  Gly  Leu  Phe  Glu  Leu  Pro  Glu
865                      870                           875                      880

Asp  Asp  Thr  Ile  Pro  Asp  Glu  Glu  His  Phe  Ile  Asp  Ile  Glu  Asp  Thr
                    885                      890                           895

Pro  Gly  Tyr  Gln  Thr  Ala  Phe  Ser  Gln  Leu  Ala  Phe  Ala  Gly  Lys  Lys
               900                      905                      910

Glu  His  Asp  Pro  Val  Gly  Gln  Met  Val  Asn  Asn  Pro  Lys  Ile  His  Leu
          915                      920                      925

Ala  Gln  Ser  Leu  His  Met  Leu  Ser  Thr  Ala  Cys  Pro  Gly  Arg  Val  Pro
     930                      935                      940

Ser  Met  Val  Ser  Thr  Ser  Leu  Asn  Ala  Glu  Ala  Leu  Gln  Tyr  Leu  Gln
945                      950                      955                      960

Gly  Tyr  Leu  Gln  Ala  Ala  Ser  Val  Thr  Leu  Leu
                    965                      970
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

CTGGTTCGGC CCACCTCTGA AGGTTCCAGA ATCGATAG     38

( 2 ) INFORMATION FOR SEQ ID NO:4:

( i ) SEQUENCE CHARACTERISTICS:

(A) LENGTH: 19 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

TAATGAGGTC TCTCACAAA  19

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GACATCCCGT CTTCCTATAT G  21

(2) INFORMATION FOR SEQ ID NO:6:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

AAGAAGCCTC ACTAGAGCAG GA  22

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO ( v ) FRAGMENT TYPE:

( v i ) ORIGINAL SOURCE:

( x i ) SEQUENCE DESCRIPTION: SEQ ID NO:7:

TGTGAAGCCG ATCGAGTGGC  20

( 2 ) INFORMATION FOR SEQ ID NO:8:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:8:

TTCAGGGACA TCCTGAAAGT  20

( 2 ) INFORMATION FOR SEQ ID NO:9:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:9:

CCCCACTGAT GGACACTGA  19

( 2 ) INFORMATION FOR SEQ ID NO:10:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:10:

CTCACCATTG ATGGAACCC  19